US006440424B1

(12) United States Patent
Sasaki et al.

(10) Patent No.: US 6,440,424 B1
(45) Date of Patent: *Aug. 27, 2002

(54) HIGH MOLECULAR WEIGHT MAJOR OUTER MEMBRANE PROTEIN OF MORAXELLA

(75) Inventors: Ken Sasaki; Robin E. Harkness, both of Willowdale; Sheena M. Loosmore, Aurora; Michel H. Klein, Willowdale, all of (CA)

(73) Assignee: Aventis Pasteur Limited, Toronto (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/483,855

(22) Filed: Jun. 7, 1995

Related U.S. Application Data

(63) Continuation-in-part of application No. 08/431,718, filed on May 1, 1995, now Pat. No. 6,335,018.

(51) Int. Cl.$^7$ .................. A61K 39/02; A61K 38/00; C07K 1/00; C07K 14/00
(52) U.S. Cl. .................. 424/251.1; 530/350; 530/412; 530/413; 530/414; 530/415; 424/190.1; 424/184.1; 424/234.1; 424/251.1; 514/2; 514/8; 930/200
(58) Field of Search .................. 530/350, 412, 530/413, 414, 415; 424/190.1, 251.1, 184.1, 234.1; 514/2, 8; 930/200

(56) References Cited

U.S. PATENT DOCUMENTS

| 4,258,029 A | | 3/1981 | Moloney et al. ............... 424/49 |
| 4,855,283 A | | 8/1989 | Lockhoff et al. ............... 514/8 |
| 5,552,146 A | | 9/1996 | Hansen ..................... 424/251.1 |
| 5,759,813 A | * | 6/1998 | Hansen et al. ........... 424/184.1 |
| 6,121,427 A | * | 9/2000 | Huang et al. ............. 435/320.1 |
| 6,214,981 B1 | * | 4/2001 | Tucker et al. |
| 6,310,190 B1 | * | 10/2001 | Hansen et al. ............. 536/23.1 |
| 6,335,018 B1 | * | 1/2002 | Sasaki et al. ............. 424/184.1 |

FOREIGN PATENT DOCUMENTS

| WO | WO A 93 03761 | 3/1883 |
| WO | WO A 91 09952 | 7/1991 |
| WO | WO A 93 10214 | 5/1993 |

OTHER PUBLICATIONS

Ostle et al. Am J. Vet. Res 47(7): 1419–1421, 1986 (Jul.).*
Van Hare, G.F., P.A. Shurin, C.D. Marchant, N.A. Cartelli, C.E. Johnson, D. Fulton, S. Carlin, and C.H. Kim. Acute otits media caused by *Branhamella catarrhalis*: biology and therapy. Rev. Infect. Dis. 9:16–27.

Chapman, A.J., D.M. Musher, S. Jonsson, J.E. Clarridge, and R.J. Wallace. 1985. Development of bactercidal antibody during *Branhamella catarrhalis* infection. J. Infect. Dis. 151:878–882.

Hager, H., A. Verghese, S. Alvarez, and S.L. Berk. 1987. *Branhamella catarrhalis* respiratory infections. Rev. Infect. Dis. 9:1140–1149.

McLeod, D.T., F. Ahmad, M.J. Croughan, and M.A. Calder. 1986. Bronchopulmonary infection due to *M. catarrhalis*. Clinical features and therapeutic response. Drugs 31(Suppl.3): 109–112.

Nicotra, B., M. Rivera, J.I. Luman, and R.J. Wallace. 1986. *Branhamella catarrhalis* as a lower respiratory tract pathogen in patients with chronic lung disease. Arch.Intern.Med. 146:890–893.

Ninane, G., J. Joly, and M. Kraytman. 1978. Bronchopulmonary infection due to *Branhamella catarrhalis* 11 cases assessed by transtracheal puncture. Br.Med.Jr. 1:276–278.

Srinivasan, G., M.J. Raff, W.C. Templeton, S.J. Givens, R.C. Graves, and J.C. Mel. 1981. *Branhamella catarrhalis* pneumonia. Report of two cases and review of the literature. Am.Rev. Respir. Dis. 123:553–555.

West, M., S.L. Berk, and J.K. Smith. 1982. *Branhamella catarrhalis* pneumonia. South.Med. J. 75:1021–1023.

Brorson, J–E., A. Axelsson, and S.E. Holm. 1976. Studies on *Branhamella catarrhalis* (*Neisseria catarrhalis*) with special reference to maxillary sinusitis. Scan. J. Infect. Dis. 8:151–155.

Evans, F.O., Jr., J.B. Sydnor, W.E.C. Moore, G.R. Moore, J.L. Manwaring, A.H. Brill, R.T. Jackson, S. Hanna, J.S. Skaar, L.V. Holdeman, G.S. Fitz–Hugh, M.A. Sande, and J.M. Gwaltney, Jr. 1975. Sinusitis of the maxillary antrum. N.Engl.J.Med. 293:735–739.

Tinkelman, D.G., and H.J. Silk. 1989. Clinical and bacteriologic features of chronic sinusitis in children. Am.J.Dis. Child. 143:938–942.

Wald, E.R., C. Byers, N. Guerra, M.Casselbrant, and D. Beste. 1989. Subacute sinusitis in children. J.Pediatr. 115:28–32.

(List continued on next page.)

*Primary Examiner*—Nita Minnifield
(74) *Attorney, Agent, or Firm*—Sim & McBurney

(57) ABSTRACT

An isolated and purified outer membrane protein of a Moraxella strain, particularly *M. catarrhalis*, has a molecular mass of about 200 kDa. The about 200 kDa outer membrane protein as well as nucleic acid molecules encoding the same are useful in diagnostic applications and immunogenic compositions, particularly for in vivo administration to a host to confer protection against disease caused by a bacterial pathogen that produces the about 200 kDa outer membrane protein or produces a protein capable of inducing antibodies in a host specifically reactive with the about 200 kDa outer membrane protein.

13 Claims, 17 Drawing Sheets

OTHER PUBLICATIONS

Wald, E.R., G.J. Milmoe, A. Bowen, J.Ledesma–Medina, N. Salamon, and C.D.Bluestone. 1981. Acute maxillary sinusitis in children. N.Engl.J.Med. 304:749–754.

Christensen, J.J., and B. Bruun. 1985. Bacteremia caused by a beta–lactamase producing strain of *Branhamella catarrhalis* . Acta.Pathol. Microbiol. Immunol. Scand. Sect.B. 93:273–275.

Craig, D.B., and P.A. Wehrle. 1983. *Branhamella catarrhalis* septic arthritis. J. Rheumatol. 10:985–986.

Gray, L.D., R.E. Van Scoy, J.P. Anhalt, and P.K.W. Yu. 1989. Wound infection caused by *Branhamella catarrhalis*. J.Clin..Microbiol. 27:818–820.

Guthrie, R., K. Bakenhaster, R.Nelson, and R. Woskobnick. 1988. *Branhamella catarrhalis* sepsis: a case report and review of the literature. J.Infect.Dis. 158:907–908.

Hiroshi, S., E.J. Anaissie, N.Khardori, and G.P. Bodey. 1988. *Branhamella catarrhalis* septicemia in patients with leukemia. Cancer 61:2315–2317.

O'Neill, J.H., and P.W. Mathieson. 1987. Meningitis due to *Branhamella catarrhalis*. Aust. N.Z. J. Med. 17:241–242.

Murphy, T.F. 1989. The surface of *Branhamella catarrhalis*: a systematic approach to the surface antigens of an emerging pathogen. Pediatr. Infect. Dis. J. 8:S75–S77.

Klingman, K.L., and T.F. Murphy. 1994. Purification and characterization of a high–molecular–weight outer membrane protein of *Moraxella*(*Branhamella*) *catarrhalis*. Infect. Immun. 62:1150–1155.

Helminen, M.E., I. Maciver, J.L. Latimer, J. Klesney–Tait, L.D. Cope, M. Paris, G.H. McCracken, Jr., and E.J. Hansen. 1994. A large, antigenically conserved protein on the surface of *Moraxella catarrhalis* is a target for protective antibodies. J. Infect. Dis. 170:867–872.

Panezutti H., O. James, E.J. Hanson, Y. Choi, R.E. Harkness, M.H. Klein and P. Chong, 1993. Identification of surface–exposed B–cell epitopes recognized by *Haemophilus influenzae* type b P1 specific monoclonal antibodies. Infec. Immun. 61: 1867–1872.

Nixon–George et al. (1990), J. Immunology 144:4798–4802.

Wiesmuller (1989), Vaccine 8:29–33.

Deres et al. (1989), Nature 342:561.

Lockhoff, O. Glycolipids as Immmunomodulators: Synthesis and Properties. 1991. Chem. Int. Ed. Engl. 30:1611–1620.

Journal of Infectious Diseases, 158 (4). 1988. 761–765., XP002013102 Bartos L C et al: "Comparison of the Outer Membrane Proteins of 50 Strains of *Branhamella–catarrhalis*" see the whole document.

Science, Apr. 14 1995, 268 (5208) P221–5, United States, XP002013103 Casey PJ: "Protein lipidation in cell signaling." see the whole document.

Murphy et al; Microbial Path. 1989, 6:159–174.

Burgess et al. J. Cell Biology 111:2129–38.

Lazar et al. Mol Cell Biology, vol. 8 No. 3: 1247–52.

Ostle et al., AM J Vet Res, vol. 47 No. 7: 1419–21.

* cited by examiner

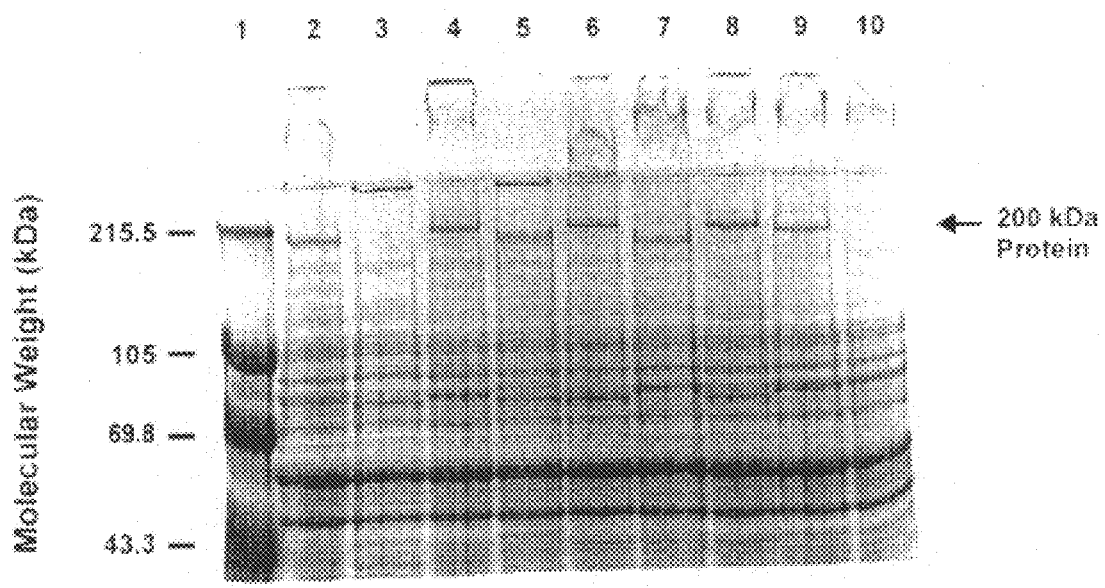

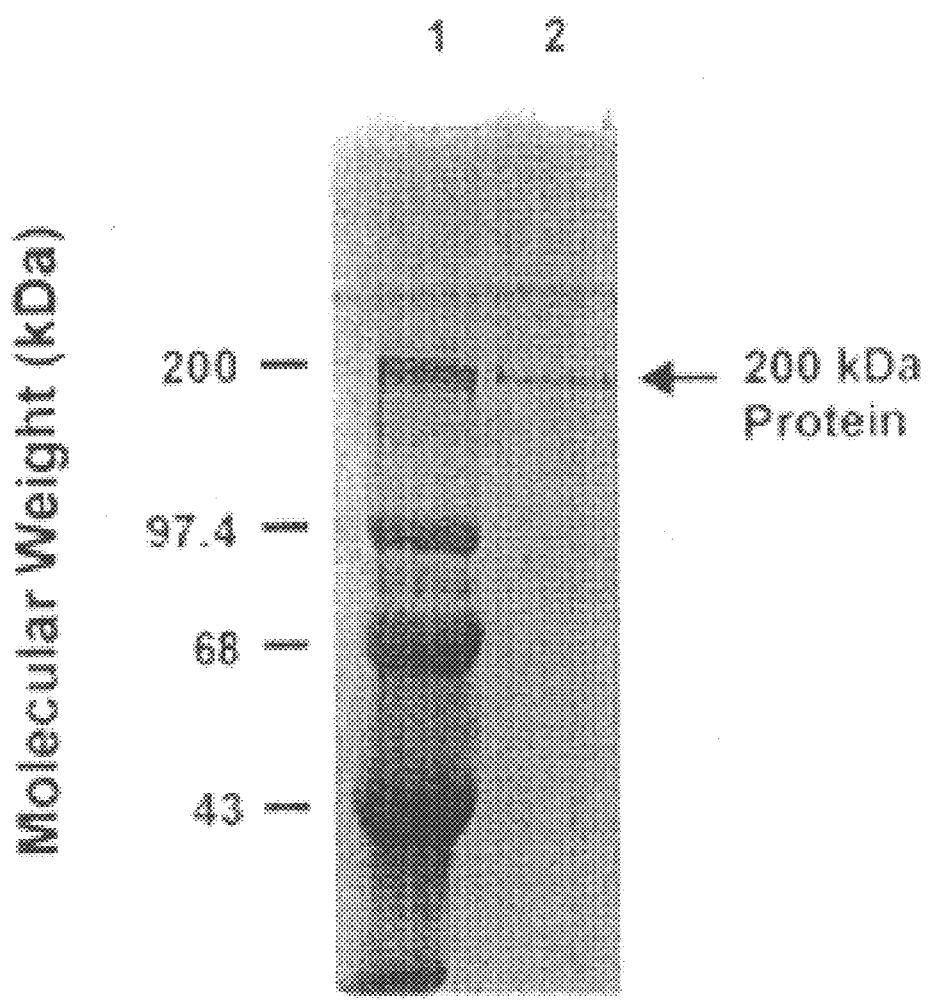

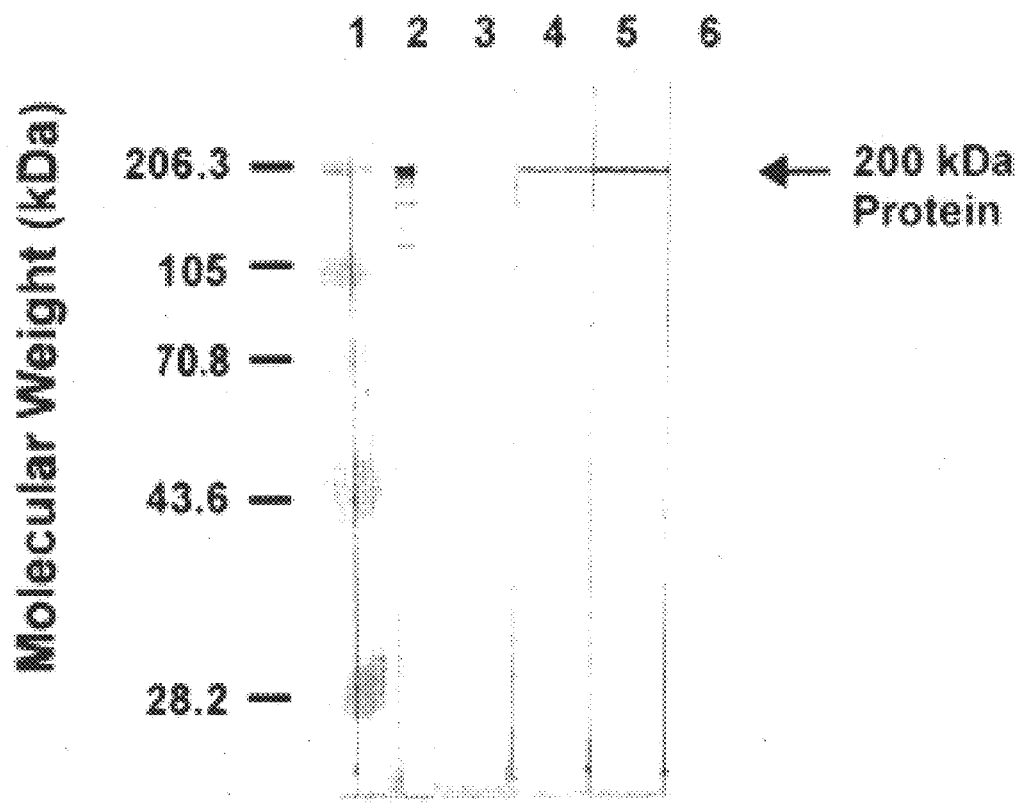

FIG.6A
Nuclectide Sequence Between SalI and NcoI

```
         10         20         30         40         50         60         70
CCATGGATAT GGGCAGGTGT GCTCGCCTGC CGTATGATGG CGATGACACC CCATTGCCC CATATCTGTA
         80         90        100        110        120        130        140
CGATTGACA TGTGATATGA TTTAACATGT GACATGATTT AACATTGTTT AATACTGTTG CCATCATTAC
        150        160        170        180        190        200        210
CATAATTTAG TAACGCATT AGTAACGCAT TTGTAAAAAT CATTGCGCCC CTTTATGTGT ATCATATGAA
        220        230        240        250        260        270        280
TAGAATATTA TGATTGTATC TGATTATTGT ATCAGAATGG TGATGCTATA TGATGATGCC TACGAGTTGA
        290        300        310        320        330        340        350
TTTGGGTTAA TCACTCTATG ATTTGATATA TTTTGAAACT AATCTATTGA CTTAAATCAC CATATGGTTA
        360        370        380        390        400        410        420
TAATTTAGCA TAATGGTAGG CTTTTTTGTAA AAATCACATC GCAATATTGT TCTACTGTTA CTACCATGCT
        430        440        450        460        470        480        490
TGAATGACGA TCCCAATCAC CAGATTCATT CAAGTGATGT GTTTGTATAC GCACCATTTA CCCTAATTAT
        500        510        520        530        540        550        560
TTCAATCAAA TGCCTATGTC AGCATGTATC ATTTTTTTAA GGTAAACCAC CATGAATGAC ATCTATAAAG
        570        580        590        600        610        620        630
TCATCTTTAA CAAAGCCACA GGCACATTTA TGGCAGTGGC AGAGTACGCC AAATCCCACA GCACGGGGGG
```

FIG.6B

```
 640        650        660        670        680        690        700
GGGTAGCTG TGCTACAGGG CAAGTTGGCA GTGTATGCAC TCTGAGCTTT GCCCGTATTG CCGCGCTCGC
 710        720        730        740        750        760        770
TGTCCTCGTG ATCGGTGCAA CGCTCAGTGG CAGTGCTTAT GCTCAAAAAA AAGATACCAA ACATATCGCA
 780        790        800        810        820        830        840
ATTGGTGAAC AAAACCAGCC AAGACGCTCA GGCACTGCCA AGGCGGACGG TGATCGAGCC ATTGCTATTG
 850        860        870        880        890        900        910
GTGAAAATGC TAACGCACAG GGCGGTCAAG CCATCGCCAT CGGTAGTAGT AATAAAACTG TCAATGGAAG
 920        930        940        950        960        970        980
CAGTTTGGAT AAGATAGGTA CCGATGCTAC GGGTCAAGAG TCCATCGCCA TCGGTGGTGA TGTAAAGGCT
 990        1000       1010       1020       1030       1040       1050
AGTGGTGATG CCTCGATTGC CATCGGTAGT GATGACTTAC ATTTGCTTGA TCAGCATGGT AATCCTAAAC
 1060       1070       1080       1090       1100       1110       1120
ATCCGAAAGG TACTCTGATT AACGATCTTA TTAACGGCCA TGCAGTATTA AAAGAAATAC GAAGCTCAAA
 1130       1140       1150       1160       1170       1180       1190
GGATAATGAT GTAAAATATA GACGCACAAC CGCAAGCGGA TGCAGTAGTA CACGCCAGTA AGCCATGTCA
 1200       1210       1220       1230       1240       1250       1260
TATGCACAGG GTCATTTTTC CAACGCCTTT GGTACACGGG CAACAGCTAA AAGTGCCTAT TCCTTGGCAG
```

FIG.6C

```
1270       1280       1290       1300       1310       1320       1330
TGGGTCTTGC CGCCACAGCC GAGGGCCAAT CTACAATCGC TATTGGTTCT GATGCAACAT CTAGCTCGTT
1340       1350       1360       1370       1380       1390       1400
GGGAGCGATA GCCCTTGGTG CAGGTACTCG TGCTCAGCTA CAGGGCAGTA TTGCCCTAGG TCAAGGTTCT
1410       1420       1430       1440       1450       1460       1470
GTTGTCACTC AGAGTGATAA TAATTCTAGA CCGGCCTATA CACCAAATAC CCAGGCACTA GACCCCAAGT
1480       1490       1500       1510       1520       1530       1540
TTCAAGCCAC CAATAATACG AAGGCGGGTC CACTTTCCAT TGGTAGTAAC TCTATCAAAC GTAAAATCAT
1550       1560       1570       1580       1590       1600       1610
CAATGTCGGT GCAGGTGTTA ATAAAACCGA TGCGGTCAAT GTGGCACAGC TAGAAGCGGT GGTGAAGTGG
1620       1630       1640       1650       1660       1670       1680
GCTAAGGAGC GTAGAATTAC TTTTCAGGGT GATGATAACA GTACTGACGT AAAAATAGGT TTGGATAATA
1690       1700       1710       1720       1730       1740       1750
CTTTAACTAT TAAAGGTGGT GCAGAGACCA ACGCATTAAC CGATAATAAT ATCGGTGTGG TAAAAGAGGC
1760       1770       1780       1790       1800       1810       1820
TGATAATAGT GGTCTGAAAG TTAAACTTGC TAAAACTTTA AACAATCTTA CTGAGGTGAA TACAACTACA
1830       1840       1850       1860       1870       1880       1890
TTAAATGCCA CAACCACAGT TAAGGTAGGT AGTAGTAGTA GTACTACAGC TGAATTATTG AGTGATAGTT
```

FIG.6D

| | | | | | | |
|---|---|---|---|---|---|---|
| 1900 TAACCTTTAC | 1910 CCAGCCCAAT | 1920 ACAGGCAGTC | 1930 AAAGCACAAG | 1940 CAAAACCGTC | 1950 TATGGCGTTA | 1960 ATGGGGTGAA |
| 1970 GTTTACTAAT | 1980 AATGCAGAAA | 1990 CAACAGCAGC | 2000 AATCGGCACT | 2010 ACTCGTATTA | 2020 CCAGAGATAA | 2030 AATTGGCTTT |
| 2040 GCTCGAGATG | 2050 GTGATGTTGA | 2060 TGAAAAACAA | 2070 GCACCATATT | 2080 TGGATAAAAA | 2090 ACAACTTAAA | 2100 GTGGGTAGTG |
| 2110 TTGCAATTAC | 2120 CATAGACAAT | 2130 GGCATTGATG | 2140 CAGGTAATAA | 2150 AAAGATCAGT | 2160 AATCTTGCCA | 2170 AAGGTAGCAG |
| 2180 TGCTAACGAT | 2190 GCGGTTACCA | 2200 TCGAACAGCT | 2210 CAAAGCCGCC | 2220 AAGCCTACTT | 2230 TAAACGCAGG | 2240 CGCTGGCATC |
| 2250 AGTGTCACAC | 2260 CTACTGAAAT | 2270 ATCAGTTGAT | 2280 GCTAAGAGTG | 2290 GCAATGTTAC | 2300 CGCCCCAACT | 2310 TACAACATTG |
| 2320 GCGTGAAAAC | 2330 CACCGAGCTT | 2340 AACAGTGATG | 2350 GCACTAGTGA | 2360 TAAATTTAGT | 2370 GTTAAGGGTA | 2380 GTGGTACGAA |
| 2390 CAATAGCTTA | 2400 GTTACCGCCG | 2410 AACATTTGGC | 2420 AAGCTATCTA | 2430 AATGAAGTCA | 2440 ATCGAACGGC | 2450 TGACAGTGCT |
| 2460 CTACAAAGCT | 2470 TTACCGTTAA | 2480 AGAAGAAGAC | 2490 GATGATGACG | 2500 CCAACGCTAT | 2510 CACCGTGGCT | 2520 AAAGATACGA |

FIG.6E

```
2530       2540       2550       2560       2570       2580       2590
CAAAAAATGC CGGCGCAGTC AGCATCTTAA AACTCAAAGG TAAAAACGGT CTAACGGTTG CTACCAAAAA 2600       2610       2620       2630       2640       2650       2660
AGATGGTACG GTTACCTTTG GGCTTAGCCA AGATAGCGGT CTGACCATTG GCAAAAGCAC CCTAAACAAC 2670       2680       2690       2700       2710       2720       2730
GATGGCTTGA CTGTTAAAGA TACCAACGAA CAAATCCAAG TCGGTGCTAA TGGCATTAAA TTTACTAATG 2740       2750       2760       2770       2780       2790       2800
TGAATGGTAG TAATCCAGGT ACTGGCATTG CAAATACCGC TCGCATTACC AGAGATAAAA TTGGCTTTGC 2810       2820       2830       2840       2850       2860       2870
TGGTTCTGAT GGTGCAGTTG ATACAAACAA ACCTTATCTT GATCAAGACA AGCTACAAGT TGGCAATGTT 2880       2890       2900       2910       2920       2930       2940
AAGATTACCA ACACTGGCAT TAACGCAGGT GGTAAAGCCA TCACAGGGCT GTCCCCAACA CTGCCTAGCA 2950       2960       2970       2980       2990       3000       3010
TTGCCGATCA AAGTAGCCGC AACATAGAAC TGGGCAATAC AATCCAAGAC AAAGACAAAT CCAACGCTGC 3020       3030       3040       3050       3060       3070       3080
CAGCATTAAT GATATATTAA ATACAGGCTT TAACCTAAAA AATAATAACA ACCCCATTGA CTTTGTCTCC 3090       3100       3110       3120       3130       3140       3150
ACTTATGACA TTGTTGACTT TGCCAATGGC AATGCCACCA CCGCCACAGT AACCCATGAT ACCGCTAACA
```

FIG.6F

```
3160        3170        3180        3190        3200        3210        3220
AAACCAGTAA  AGTGGTATAT  GATGTGAATG  TGGATGATAC  AACCATTCAT  CTAACAGGCA  CTGATGACAA 3230        3240        3250        3260        3270        3280        3290
TAAAAAACTT  GGCGTCAAAA  CCACCAAACT  GAACAAAACA  AGTGCTAATG  GTAATACAGC  AACTAACTTT 3300        3310        3320        3330        3340        3350        3360
AATGTTAACT  CTAGTGATGA  AGATGCCCTT  GTTAACGCCA  AAGACATCGC  CGAAAATCTA  AACACCCTAG 3370        3380        3390        3400        3410        3420        3430
CCAAGGAAAT  TCACACCACC  AAAGGCACAG  CAGACACCGC  CCTACAAACC  TTTACCGTTA  AAAAGGTAGA 3440        3450        3460        3470        3480        3490        3500
TGAAAATAAT  AATGCTGATG  ACGCCAACGC  CATCACCGTG  GGTCAAAAGA  ACGCAAATAA  TCAAGTCAAC 3510        3520        3530        3540        3550        3560        3570
ACCCTAACAC  TCAAAGGTGA  AAACGGTCTT  AATATTAAAA  CCGACAAAAA  TGGTACGGTT  ACCTTTGGCA 3580        3590        3600        3610        3620        3630        3640
TTAACACCAC  AAGCGGTCTT  AAAGCCGGCA  AAAGCACCCT  AAACGACGGT  GGCTTGTCTA  TTAAAAACCC 3650        3660        3670        3680        3690        3700        3710
CACTGGTAGC  GAACAAATCC  AAGTCGGTGC  TGATGGCGTG  AAGTTTGCCA  AGGTTAATAA  TAATGGTGTT 3720        3730        3740        3750        3760        3770        3780
GTAGGTGCTG  GCATTGATGG  CACAACTCGC  ATTACCAGAG  ATGAAATTGG  CTTTACTGGG  ACTAATGGCT
```

FIG. 6G

```
3790        3800        3810        3820        3830        3840        3850
CACTTGATAA  AAGCAAACCC  CACCTAAGCA  AAGACGGCAT  TAACGCAGGT  GGTAAAAAGA  TTACCAACAT 3860        3870        3880        3890        3900        3910        3920
TCAATCAGGT  GAGATTGCCC  AAAACAGCCA  TGATGCTGTG  ACAGGCGGCA  AGATTTATGA  TTTAAAAACC 3930        3940        3950        3960        3970        3980        3990
GAACTTGAAA  ACAAAATCAG  CAGTACTGCC  AAAACAGCAC  AAAACTCATT  ACACGAATTC  TCAGTAGCAG 4000        4010        4020        4030        4040        4050        4060
ATGAACAAGG  TAATAACTTT  ACGGTTAGTA  ACCCTTACTC  CAGTTATGAC  ACCTCAAAGA  CCTCTGATGT 4070        4080        4090        4100        4110        4120        4130
CATCACCTTT  GCAGGTGAAA  ACGGCATTAC  CACCAAGGTA  AATAAAGGTG  TGGTGCGTGT  GGGCATTGAC 4140        4150        4160        4170        4180        4190        4200
CAAACCAAAG  GCTTAACCAC  GCCTAAGCTG  ACCGTGGGTA  ATAATAATGG  CAAAGGCATT  GTCATTGACA 4210        4220        4230        4240        4250        4260        4270
GCCAAAATGG  TCAAAATACC  ATCACAGGAC  TAAGCAACAC  TCTAGCTAAT  GTTACCAATG  ATAAAGGTAG 4280        4290        4300        4310        4320        4330        4340
CGTACGCACC  ACAGAACAGG  GCAATATAAT  CAAAGACGAA  GACAAAACCC  GTGCCGCCAG  CATTGTTGAT 4350        4360        4370        4380        4390        4400        4410
GTGCTAAGCG  CAGGCTTTAA  CTTGCAAGGC  AATGGTGAAG  CGGTTGACTT  TGTCTCCACT  TATGACACCG
```

FIG.6H

```
4420       4430       4440       4450       4460       4470       4480
TCAACTTTGC CGATGGCAAT GCCACCACCG CTAAGGTGAC CTATGATGAC ACAAGCAAAA CCAGTAAAGT
4490       4500       4510       4520       4530       4540       4550
GGTCTATGAT GTCAATGTGG ATGATACAAC CATTGAAGTT AAAGATAAAA AACTTGGCGT AAAAACCACC
4560       4570       4580       4590       4600       4610       4620
ACATTGACCA GTACTGGCAC AGGTGCTAAT AAATTTGCCC TAAGCAATCA AGCTACTGGC GATGCGCTTG
4630       4640       4650       4660       4670       4680       4690
TCAAGGCCAG TGATATCGTT GCTCATCTAA ACACCTTATC TGGCGACATC CAAACTGCCA AAGGGGCAAG
4700       4710       4720       4730       4740       4750       4760
CCAAGCGAAC AACTCAGCAG GCTATGTGGA TGCTGATGGC AATAAGGTCA TCTATGACAG TACCGATAAC
4770       4780       4790       4800       4810       4820       4830
AAGTACTATC AAGCCAAAAA TGATGGCACA GTTGATAAAA CCAAAGAAGT TGCCAAAGAC AAACTGGTCG
4840       4850       4860       4870       4880       4890       4900
CCCAAGCCCA AACCCCAGAT GGCACATTGG CTCAAAATGA TGTCAAATCA GTCATTAACA AAGAACAAGT
4910       4920       4930       4940       4950       4960       4970
AAATGATGCC AAGGCATCAA TGAAGACAAC GCCTTTGTTA AGGACTTGA AAAGCCGCT
4980       4990       5000       5010       5020       5030       5040
TCTGATAACA AAACCAAAAA CGCCGCAGTA ACTGTGGGTG ATTTAAATGC CGTTGCCCAA ACACCGCTGA
```

FIG.6I

```
      5050        5060        5070        5080        5090        5100        5110
CCTTTGCAGG  GGATACAGGC  ACAACGGCTA  AAAAACTGGG  CGAGACTTTG  ACCATCAAAG  GTGGGCAAAC
      5120        5130        5140        5150        5160        5170        5180
AGACACCAAT  AAGCTAACCG  ATAATAACAT  CGGTGTGGTA  GCAGGTACTG  ATGGCTTCAC  TGTCAAACTT
      5190        5200        5210        5220        5230        5240        5250
GCCAAAGACC  TAACCAATCT  TAACAGCGTT  AATGCAGGTG  GCACCAAAAT  TGATGACAAA  GGCGTGTCTT
      5260        5270        5280        5290        5300        5310        5320
TTGTAGACTC  AAGCGGTCAA  GCCAAAGCAA  ACACCCCTGT  GCTAAGTGCC  AATGGGCTGG  ACCTGGGTGG
      5330        5340        5350        5360        5370        5380        5390
CAAGGTCATC  AGTAATGTGG  GCAAAGGCAC  AAAAGATACC  GACGCTGCCA  ATGTACAACA  GTTAAACGAA
      5400        5410        5420        5430        5440        5450        5460
GTACGCAACT  TGTTGGGTCT  TGGTAATGCT  GGTAATGATA  ACGCTGACGG  CAATCAGGTA  AACATTGCCG
      5470        5480        5490        5500        5510        5520        5530
ACATCAAAAA  AGACCCAAAT  TCAGGTTCAT  CATCCTAACCG  CACTGTCATC  AAAGCAGGCA  CGGTACTTGG
      5540        5550        5560        5570        5580        5590        5600
CGGTAAAGGT  AATAACGATA  CCGAAAAACT  TGCCCACTGGT  GGTATACAAG  TGGGCGTGGA  TAAAGACGGC
      5610        5620        5630        5640        5650        5660        5670
AACGCTAACG  GCGATTTAAG  CAATGTTTGG  GTCAAAACCC  AAAAGATGG   CAGCAAAAAA  GCCCTGCTCG
      5680        5690        5700        5710        5720        5730        5740
CCACTTATAA  CGCCGCAGGT  CAGACCAACT  ATTTGACCAA  CAACCCCGCA  GAAGCCATTG  ACAGAATAAA
```

FIG.6J

| | | | | | | |
|---|---|---|---|---|---|---|
| 5750 TGAACAAGGT | 5760 ATCCGCTTCT | 5770 TCCATGTCAA | 5780 CGATGGCAAT | 5790 CAAGAGCCTG | 5800 TGGTACAAGG | 5810 GCGTAACGGC |
| 5820 ATTGACTCAA | 5830 GTGCCTCAGG | 5840 CAAGCACTCA | 5850 GTGGCGATAG | 5860 GTTTCCAGGC | 5870 CAAGGCAGAT | 5880 GGTGAAGCCG |
| 5890 CCGTTGCCAT | 5900 AGGCAGACAA | 5910 ACCCAAGCAG | 5920 GCAACCAATC | 5930 CATCGCCATC | 5940 GGTGATAACG | 5950 CACAAGCCAC |
| 5960 GGGCGATCAA | 5970 TCCATCGCCA | 5980 TCGGTACAGG | 5990 CAATGTGGTA | 6000 GCAGGTAAGC | 6010 ACTCTGGTGC | 6020 CATCGGCGAC |
| 6030 CCAAGCACTG | 6040 TTAAGGCTGA | 6050 TAACAGTTAC | 6060 AGTGTGGGTA | 6070 ATAACAACCA | 6080 GTTTACCGAT | 6090 GCCACTCAAA |
| 6100 CCGATGTCTT | 6110 TGGTGTGGGC | 6120 AATAACATCA | 6130 CCGTGACCGA | 6140 AAGTAACTCG | 6150 GTTGCCTTAG | 6160 GTTCAAACTC |
| 6170 TGCCATCAGT | 6180 GCAGGCACAC | 6190 ACGCAGGCAC | 6200 ACAAGCCAAA | 6210 AAATCTGACG | 6220 GCACAGCAGG | 6230 TACAACCACC |
| 6240 ACAGCAGGTG | 6250 CAACCGGTAC | 6260 GGTTAAAGGC | 6270 TTTGCTGGAC | 6280 AAACGGCGGT | 6290 TGGTGCGGTC | 6300 TCCGTGGGTG |
| 6310 CCTCAGGTGC | 6320 TGAACGCCGT | 6330 ATCCAAAATG | 6340 TGGCAGCAGG | 6350 TGAGGTCAGT | 6360 GCCACCAGCA | 6370 CCGATGCGGT |
| 6380 CAATGGTAGC | 6390 CAGTTGTACA | 6400 AAGCCACCCA | 6410 AAGCATTGCC | 6420 AACGCAACCA | 6430 ATGAGCTTGA | 6440 CCATCGTATC |

FIG.6K

```
6450       6460       6470       6480       6490       6500       6510
CACCAAAACG AAAATAAGGC CAATGCAGGG ATTTCATCAG CGATGGCGAT GGCGTCCATG CCACAAGCCT 6520       6530       6540       6550       6560       6570       6580
ACATTCCTGG CAGATCCATG GTTACCGGGG GTATTGCCAC CCACAACGGT CAAGGTGCGG TGGCAGTGGG 6590       6600       6610       6620       6630       6640       6650
ACTGTCGAAG CTGTCGGATA ATGGTCAATG GGTATTTAAA ATCAATGGTT CAGCCGATAC CCAAGGCCAT 6660       6670       6680       6690       6700       6710       6720
GTAGGGGCGG CAGTTGGTGC AGGTTTTCAC TTTTAAGCCA TAAATCGCAA GATTTTACTT AAAAATCAAT 6730       6740       6750       6760       6770       6780       6790
CTCACCATAG TTGTATAAAA CAGCATCAGC ATCAGTCATA TTACTGATGC TGATGTTTTT TATCACTTAA 6800       6810       6820       6830       6840       6850       6860
ACCATTTTAC CGCTCAAGTG ATTCTCTTTC ACCATGACCA AATCGCCATT GATCATAGGT AAACTTATTG 6870       6880       6890       6900       6910       6920       6930
AGTAAATTTT ATCAATGTAG TTGTTAGATA TGGTTAAAAT TGTGCCATTG ACCAAAAAAT GACCGATTTA 6940       6950       6960       6970
TCCCGAAAAT TTCTGATTAT GATCCGTTGA CCTGCAGGTC GAC
```

HIGH MOLECULAR WEIGHT MAJOR OUTER MEMBRANE PROTEIN OF MORAXELLA

REFERENCE TO RELATED APPLICATION

This application is a continuation-in-part of U.S. patent application Ser. No. 08/431,718 filed May 1, 1995 now U.S. Pat. No. 6,335,018.

FIELD OF THE INVENTION

The present invention relates to the field of immunology and is particularly concerned with outer membrane proteins from Moraxella, methods of production thereof, genes encoding such proteins and uses thereof.

BACKGROUND OF THE INVENTION

Otitis media is the most common illness of early childhood with approximately 70% of all children suffering at least one bout of otitis media before the age of seven. Chronic otitis media can lead to hearing, speech and cognitive impairment in children. It is caused by bacterial infection with *Streptococcus pneumoniae* (approximately 50%), non-typable *Haemophilus influenzae* (approximately 30%) and *Moraxella* (Branhamella) *catarrhalis* (approximately 20%). In the United States alone, treatment of otitis media costs between one and two billion dollars per year for antibiotics and surgical procedures, such as tonsillectomies, adenoidectomies and insertion of tympanostomy tubes. Because otitis media occurs at a time in life when language skills are developing at a rapid pace, developmental disabilities specifically related to learning and auditory perception have been documented in youngsters with frequent otitis media.

*M. catarrhalis* mainly colonizes the respiratory tract and is predominantly a mucosal pathogen. Studies using cultures of middle ear fluid obtained by tympanocentesis have shown that *M. catarrhalis* causes approximately 20% of cases of otitis media (ref. 1—Throughout this application, various references are referred to in parenthesis to more fully describe the state of the art to which this invention pertains. Full bibliographic information for each citation is found at the end of the specification, immediately preceding the claims. The disclosures of these references are hereby incorporated by reference into the present disclosure).

The incidence of otitis media caused by *M. catarrhalis* is increasing. As ways of preventing otitis media caused by pneumococcus and nontypeable *H. influenzae* are developed, the relative importance of *M. catarrhalis* as a cause of otitis media can be expected to further increase.

*M. catarrhalis* is also an important cause of lower respiratory tract infections in adults, particularly in the setting of chronic bronchitis and emphysema (refs. 2, 3, 4, 5, 6, 7, and 8). *M. catarrhalis* also causes sinusitis in children and adults (refs. 9, 10. 11, 12, and 13) and occasionally causes invasive disease (refs. 14, 15, 16, 17, 18, and 19).

Like other Gram-negative bacteria, the outer membrane of *M. catarrhalis* consists of phospholipids, lipopolysaccharide (LPS), and outer membrane proteins (OMPs). Eight of the *M. catarrhalis* OMPs have been identified as major components. These are designated by letters A through H, beginning with OMP A which has a molecular mass of 98 kDa to OMP H which has a molecular mass of 21 kDa (ref. 20).

Recently, a high-molecular-weight outer membrane protein of *M. catarrhalis* was purified and characterized (ref. 21). The apparent molecular mass of this protein varies from 350 kDa to 720 kDa as judged by sodium dodecyl sulfate-polyacrylamide gel electrophoresis (SDS-PAGE). This protein appears to be an oligomer of much smaller proteins or subunits thereof of molecular mass 120 to 140 kDa and is antigenically conserved among strains of Moraxella.

A similar protein named UspA was also reported to be present on the surface of this species of bacteria with an apparent molecular mass of 300 to 400 kDa (ref. 22). Judging from the molecular mass, these two proteins may be the same.

*M. catarrhalis* infection may lead to serious disease. It would be advantageous to provide other outer membrane proteins for *M. catarrhalis* and genes encoding such proteins for use as antigens in immunogenic preparations including vaccines, carriers for other antigens and immunogens and the generation of diagnostic reagents.

SUMMARY OF THE INVENTION

The present invention is directed towards the provision of purified and isolated major outer membrane protein of *Moraxella catarrhalis* and other Moraxella strains, having an apparent molecular mass of about 200 kDa.

In accordance with one aspect of the invention, there is provided an isolated and purified, outer membrane protein of a Moraxella strain having a molecular weight of about 200 kDa, as determined by SDS-PAGE, or a fragment or an analog thereof. The outer membrane protein may be substantially in its native conformation (so as to have substantially retained the characteristic immunogenicity of the outer membrane protein in the Moraxella strain) and may be isolated from a *M. catarrhalis* strain, such as from *M. catarrhalis* 4223. Such isolated and purified about 200 kDa outer membrane protein is substantially free from non-200 kDa outer membrane protein, phospholipids and lipopolysaccharide of Moraxella. The about 200 kDa outer membrane protein is at least about 70 wt % pure, preferably at least about 90 wt % pure, and may be in the form of an aqueous solution thereof.

The present invention also provides a purified and isolated nucleic acid molecule encoding an outer membrane protein of a strain of Moraxella having a molecular mass of about 200 kDa, as determined by SDS-PAGE, or a fragment or an analog of the outer membrane protein. The protein encoded by the nucleic acid molecule may encode a protein containing the amino acid sequence NH$_2$-Asn-Val-Lys-Ser-Val-Ile-Asn-Lys-Glu-Gln-Val-Asn-Asp-Ala-Asn-Lys-x-Gln-Gly-Ile (SEQ ID No: 2) for *Moraxella catarrhalis* strain 4223 or containing the corresponding amino acid sequence from other Moraxella strains.

In a further aspect of the present invention, there is provided a purified and isolated nucleic acid molecule having a sequence selected from the group consisting of (a) the sequence set out in FIG. 6 (SEQ ID No: 1), or the complementary sequence thereto; (b) a sequence encoding an about 200 kDa protein of a strain of Moraxella and containing the amino acid sequence NH$_2$-Asn-Val-Lys-Ser-Val-Ile-Asn-Lys-Glu-Gln-Val-Asn-Asp-Ala-Asn-Lys-x-Gln-Gly-Ile (SEQ ID No: 2), or the complementary sequence thereto; and (c) a nucleotide sequence which hybridizes under stringent conditions to any one of the sequences defined in (a) or (b). The nucleic acid preferably defined in (c) has at least about 90% sequence identity with any one of the sequences defined in (a) or (b).

The nucleic acid molecules provided herein may be included in a vector adapted for transformation of a host.

The nucleic acid molecules provided herein also may be included in an expression vector adapted for transformation of a host along with expression means operatively coupled to the nucleic acid molecule for expression by the host of the about 200 kDa outer membrane protein of a strain of Moraxella or the fragment or the analog of the outer membrane protein. A transformed host containing the expression vector is included within the invention, along with a recombinant outer membrane protein or fragment or analog thereof producible by the transformed host.

The expression means may include a nucleic acid portion encoding a leader sequence for secretion from the host of the outer membrane protein or the fragment or the analog of the outer membrane protein. The expression means may include a nucleic acid portion encoding a lipidation signal for expression from the host of a lipidated form of the outer membrane protein or the fragment or analog thereof.

The present invention further includes a live vector for delivery of the outer membrane protein of the invention or a fragment or analog thereof, comprising a vector containing the nucleic acid molecule provided herein. The live vector may be selected from the group consisting of *E. coli*, Salmonella, BCG, adenovirus, poxvirus, vaccinia and poliovirus.

In accordance with a further aspect of the present invention, there is provided a peptide having no less than six amino acids and no more than 150 amino acids and containing an amino acid sequence corresponding to a portion only of the outer membrane protein of the invention, or a fragment or analog thereof. The peptide may be one having the amino acid sequence $NH_2$-Asn-Val-Lys-Ser-Val-Ile-Asn-Lys-Glu-Gln-Val-Asn-Asp-Ala-Asn-Lys-x-Gln-Gly-Ile (SEQ ID No: 2) for the *Moraxella catarrhalis* 4283 strain or the amino acid sequence for the corresponding peptide for other strains of Moraxella.

The present invention also provides an immunogenic composition comprising an immunoeffective amount of an active component, which may be the outer membrane protein or fragment or analog thereof, nucleic acid molecules, recombinant outer membrane proteins, fragments or analogs thereof, live vectors, and/or peptides as provided herein, along with a pharmaceutically acceptable carrier therefor with the active component producing an immune response when administered to a host, which may be a primate, particularly a human. The immunogenic composition may be formulated as a vaccine for in vivo administration to a host to confer protection against diseases caused by a bacterial pathogen that produces the about 200 kDa outer membrane protein or produces a protein capable of inducing antibodies in the host specifically reactive with the about 200 kDa outer membrane protein. In particular, the bacterial pathogen is a strain of Moraxella, particularly *M. catarrhalis*. The immunogenic composition may be formulated as a microparticle capsule, ISCOM or liposome preparation. The immunogenic composition may be used in combination with a targeting molecule for delivery to specific cells of the immune system as to mucosal surfaces. The immunogenic compositions of the invention (including vaccines) may further comprise at least one other immunogenic or immunostimulating material and the immunostimulating material may be at least one adjuvant. Suitable adjuvants for use in the present invention include, (but are not limited to) aluminum phosphate, aluminum hydroxide, QS21, Quil A, calcium phosphate, calcium hydroxide, zinc hydroxide, a glycolipid analog, and octadecyl ester of an amino acid, a muramyl dipeptide and a lipoprotein. Advantageous combinations of adjuvants are described in copending U.S. patent application Ser. No. 261,194 filed Jun. 16, 1994, assigned to the assignee hereof and the disclosure of which is incorporated herein by reference. The invention further includes an antibody specific for the outer membrane protein provided herein producible by immunizing a host with an immunogenic composition provided herein.

In a further aspect of the invention, there is provided a method of generating an immune response in a host comprising administering thereto an immuno-effective amount of the immunogenic composition as provided herein. The immune response may be a humoral or a cell-mediated immune response. The immune response may provide protection to the host against diseases caused by a bacterial pathogen that produces the about 200 kDa outer membrane protein or produces a protein capable of inducing antibodies in the host specifically reactive with the about 200 kDa outer membrane protein. Hosts in which protection against disease may be conferred include primates including humans.

The present invention provides, in an additional aspect thereof, a method of producing a vaccine comprising administering the immunogenic composition provided herein to a test host to determine an amount and a frequency of administration of the active component to confer protection against disease caused by a bacterial pathogen that produces the about 200 kDa outer membrane protein or produces a protein capable of inducing antibodies in the host specifically reactive with the about 200 kDa outer membrane protein, and formulating the active component in a form suitable for administration to a treated host in accordance with said determined amount and frequency of administration. The treated host may be a human.

A further aspect of the present invention provides a method of determining the presence of nucleic acid encoding an outer membrane protein of a strain of Moraxella having a molecular mass of about 200 kDa, as determined by SDS-PAGE, in a sample, comprising the steps of:

(a) contacting the sample with the nucleic acid molecule provided herein to produce duplexes comprising the nucleic acid molecules and any said nucleic acid molecule encoding the outer membrane protein present in the sample and specifically hybridizable therewith; and (b) determining the production of the duplexes.

In yet a further aspect of the invention, there is provided a method of determining the presence of antibodies specifically reactive with outer membrane protein of a strain of Moraxella having a molecular mass of about 200 kDa, in a sample, comprising the steps of:

(a) contacting the sample with the outer membrane protein as provided herein to produce complexes comprising the outer membrane protein and any said antibodies present in the sample-specifically reactive therewith; and (b) determining production of the complexes.

In a further aspect of the invention, there is also provided a method of determining the presence of an outer membrane protein if a strain of Moraxella having a molecular mass of about 200 kDa, in a sample comprising the steps of:

(a) immunizing a subject with the immunogenic composition as provided herein, to produce antibodies specific for the outer membrane protein;

(b) contacting the sample with the antibodies to produce complexes comprising any outer membrane protein present in the sample and said outer membrane protein specific antibodies; and (c) determining production of the complexes.

The outer membrane protein may be part of a *Moraxella catarrhalis* strain.

The present invention provides, in a yet further aspect, a diagnostic kit for determining the presence of nucleic acid encoding an outer membrane protein of a strain of Moraxella having a molecular mass of about 200 kDa, as determined by SDS-PAGE, in a sample, comprising:
(a) the nucleic acid molecule as provided herein;
(b) means for contacting the nucleic acid with the sample to produce duplexes comprising the nucleic acid molecule and any said nucleic acid present in the sample and hybridizable with the nucleic acid molecule; and
(c) means for determining production of the duplexes.

In yet a further aspect of the invention, there is provided a diagnostic kit for determining the presence of antibodies in a sample specifically reactive with the outer membrane protein of a strain of Moraxella having a molecular mass of about 200 kDa, as determined by SDS-PAGE, comprising:
(a) the outer membrane protein as provided herein;
(b) means for contacting the outer membrane protein with the sample to produce complexes comprising the outer membrane protein and any said antibodies present in the sample; and
(c) means for determining production of the complexes.

The invention also provides a diagnostic kit for detecting the presence of an outer membrane protein of a strain of Moraxella having a molecular mass of about 200 kDa, in a sample, comprising:
(a) an antibody specific for the about 200 kDa outer membrane protein as provided herein;
(b) means for contacting the antibody with the sample to produce a complex comprising the outer membrane protein and outer membrane-specific antibody; and
(c) means for determining production of the complex.

In a further aspect of the invention, there is provided a method of producing an isolated and purified outer membrane protein of a strain of Moraxella having a molecular mass of about 200 kDa, is determined by SDS-PAGE, comprising the steps of:
(a) providing a cell mass of the Moraxella strain;
(b) disrupting the cell mass to provide a cell lysate;
(c) fractionating the cell lysate to provide a fraction containing the outer membrane protein substantially free from other cell lysate components, and
(d) recovering said outer membrane protein.

The bacterial strain may be *Moraxella catarrhalis*. The cell lysate may be fractionated by gel electrophoresis.

In this application, the term "about 200 kDa protein" is used to define a family of outer membrane proteins of *M. catarrhalis* having molecular mass of between about 160 and 230 kDa and includes proteins having variations in their amino acid sequences including those naturally occurring in various strains of Moraxella. The purified and isolated DNA molecules comprising a gene having an open reading frame of the about 200 kDa protein of the present invention also include those encoding functional analogs of the about 200 kDa protein. In this application, a first protein or peptide is a "functional analog" of a second protein if the first protein is immunologically related to and/or has the same function as the second protein or peptide. The functional analog may be, for example, a fragment of the protein or a substitution, addition or deletion mutant thereof.

Advantages of the present invention include:
a method for isolating purified about 200 kDa outer membrane protein of a Moraxella strain that produces the outer membrane protein, including *Moraxella catarrhalis*;

an isolated and purified about 200 kDa outer membrane protein isolatable from a Moraxella strain; and diagnostic kits and immunological reagents for specific identification of Moraxella and hosts infected thereby.

BRIEF DESCRIPTION OF THE DRAWINGS

FIG. 2 shows a comparative analysis of cell proteins from a number of *M. catarrhalis* strains by SDS-PAGE analysis. The identification of the lanes and the sources of the proteins are given in Example 4 below;

FIG. 3 shows an analysis of isolated and purified about 200 kDa outer membrane protein of *M. catarrhalis* by SDS-PAGE. The identification of the lanes is given in Example 4 below;

FIG. 4 shows the specific recognition of about 200 kDa outer membrane protein by anti-peptide antiserum. The identification of the lanes and antiserum are given in Example 8 below;

FIG. 6 shows the nucleotide sequence (SEQ ID No: 1) of the gene having an open reading frame of the about 200 kDa outer membrane protein of *M. catarrhalis*;

GENERAL DESCRIPTION OF INVENTION

Figure 1A:
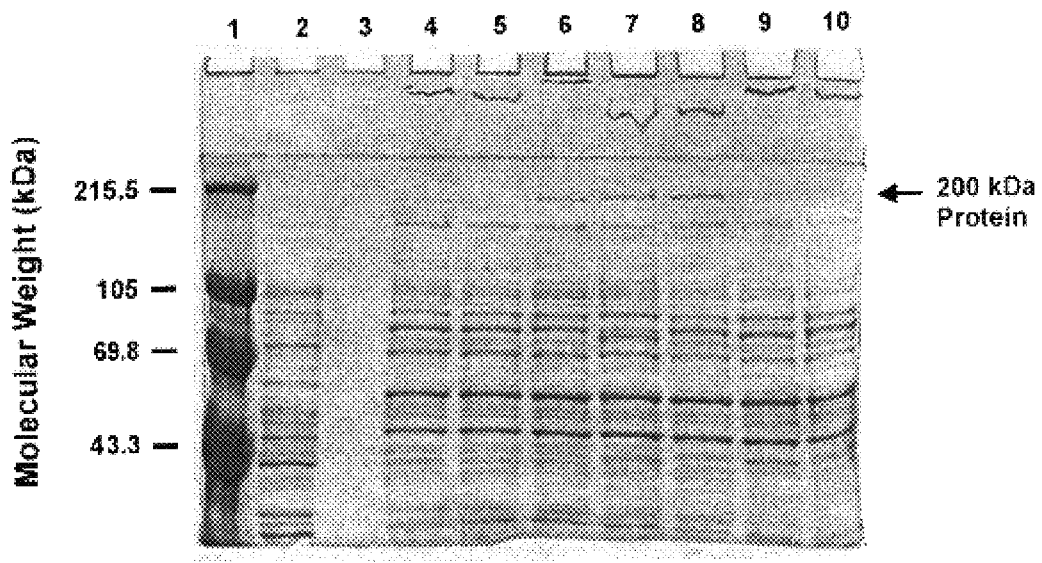
FIGS. 1A and 1B show an analysis of *Moraxella catarrhalis* cell proteins by SDS-PAGE. The identification of the lanes and the sources of the proteins are given in Example 2 below.
Figure 1B:
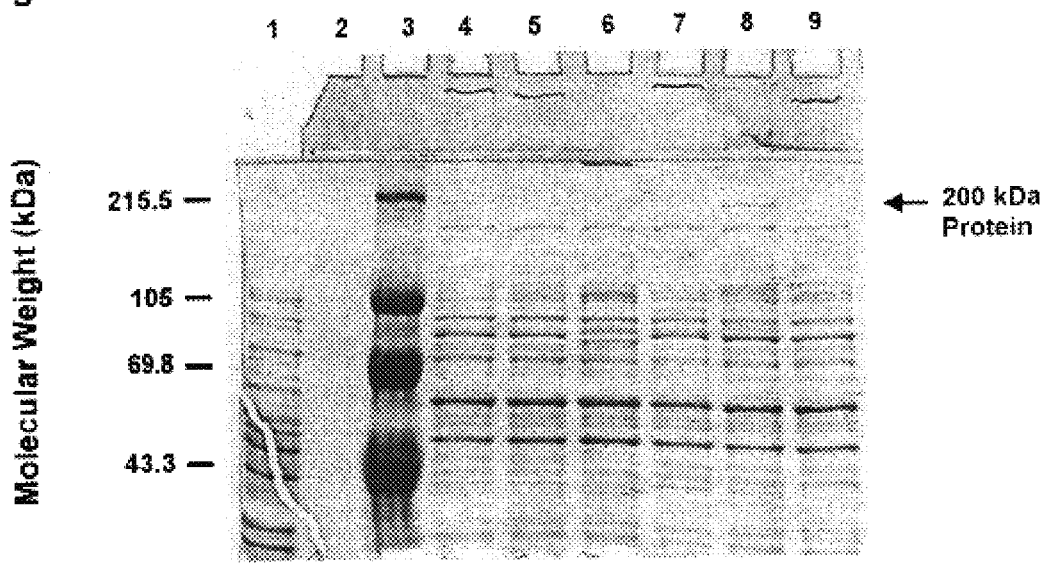

Referring to FIGS. 1A and 1B and FIG. 2, there is illustrated the separation of a novel outer membrane protein from a variety of strains of *M. catarrhalis* having a molecular mass about 200 kDa. FIG. 3 shows the isolated and purified outer membrane protein.

The purified protein was eluted from the gel and used to raise antibodies in guinea pigs. The antibodies specifically recognize only strains of *M. catarrhalis* which produce the outer membrane protein (Table I below).

Referring to FIG. 4, there is shown the recognition of the about 200 kDa outer membrane protein by antibodies raised in guinea pigs to a synthesized peptide corresponding to an internal fragment of the about 200 kDa protein. The synthesized peptide had the amino acid sequence $NH_2$-Asn-Val-Lys-Ser-Val-Ile-Asn-Lys-Glu-Gln-Val-Asn-Asp-Ala-Asn-Lys (SEQ ID No: 3).

Figure 5:
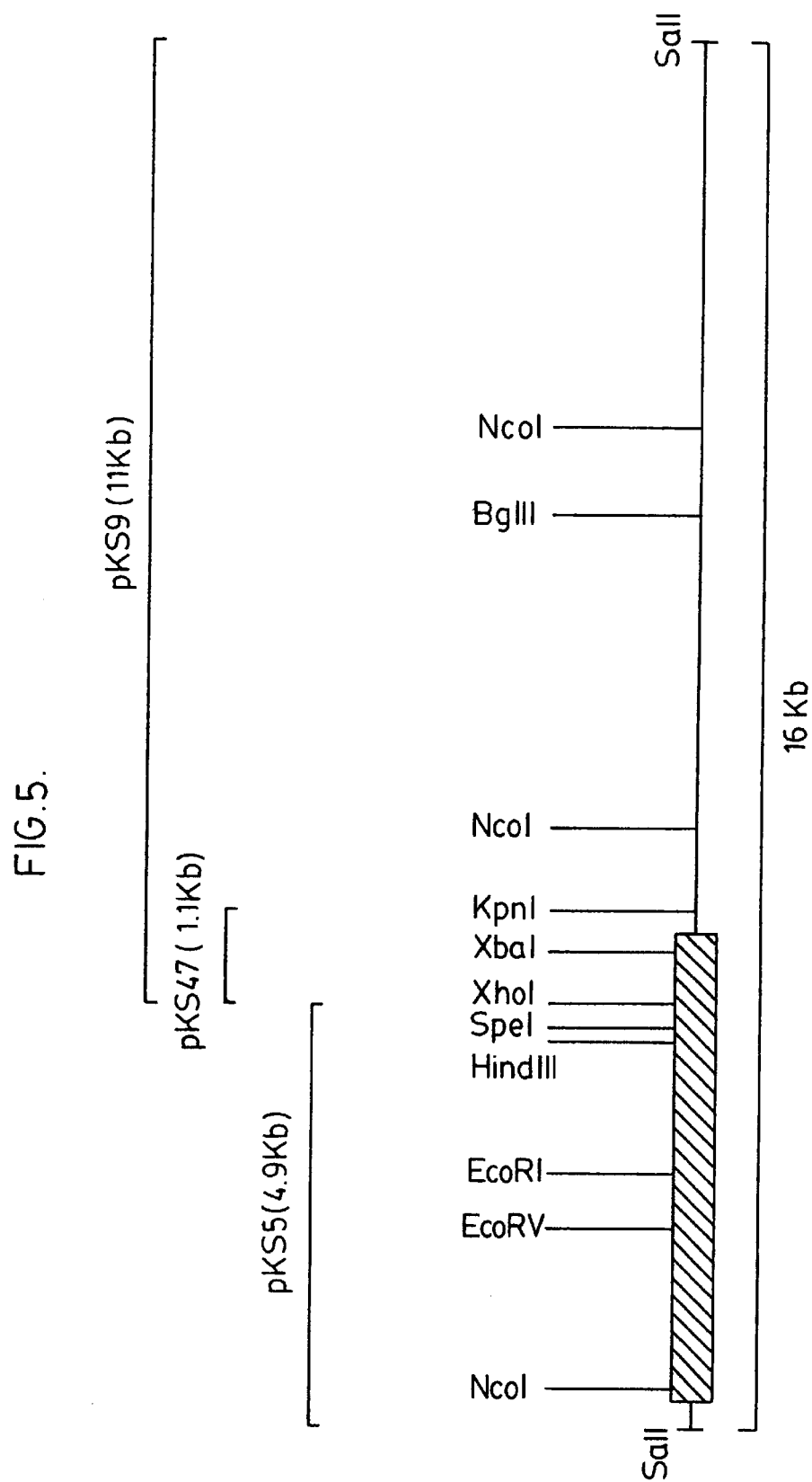
FIG. 5 shows restriction maps of clones containing a gene having an open reading frame of the about 200 kDa outer membrane protein of *M. catarrhalis*. An open reading frame of the about 200 kDa outer membrane protein is indicated by the hatched box.

Referring to FIG. 5, there is shown restriction maps of clones containing a gene having an open reading frame of the about 200 kDa outer membrane protein. The nucleotide sequence (SEQ ID No: 1) of the gene having an open reading frame coding for the about 200 kDa outer membrane protein as shown in FIG. 6.

In one embodiment of the present invention, the isolated and purified about 200 kDa outer membrane protein as provided herein is useful for generating antibodies that can be used to specifically distinguish *M. catarrhalis* from other bacterial pathogens that cause otitis media and other diseases. Thus referring to FIG. 7, there is illustrated an immunoblot showing the specific reactivity of a guinea pig monospecific anti-200 kDa outer membrane protein antiserum produced by immunizing mice with the purified about 200 kDa outer membrane protein as provided herein. The bacterial lysates analyzed were as follows:

| Lane | Bacterium | Source |
| --- | --- | --- |
| 1. | Molecular Weight Standard | |
| 2. | M. catarrhalis 4223 | middle ear fluid |
| 3. | M. catarrhalis RH408 | non-clumping variant of strain 4223 |
| 4. | H. influenzae, MinnA strain | meningitis isolate |
| 5. | non-typable H. influenzae, SB12 strain | otitis media isolate |
| 6. | non-typable H. influenzae, SB33 strain | otitis media isolate |
| 7. | S. pneumoniae type 6 | ATCC 6306 |
| 8. | S. pneumoniae type 14 | ATCC 6314 |
| 9. | P. aeruginosa | |
| 10. | E. coli DH5α | |

Figure 7:
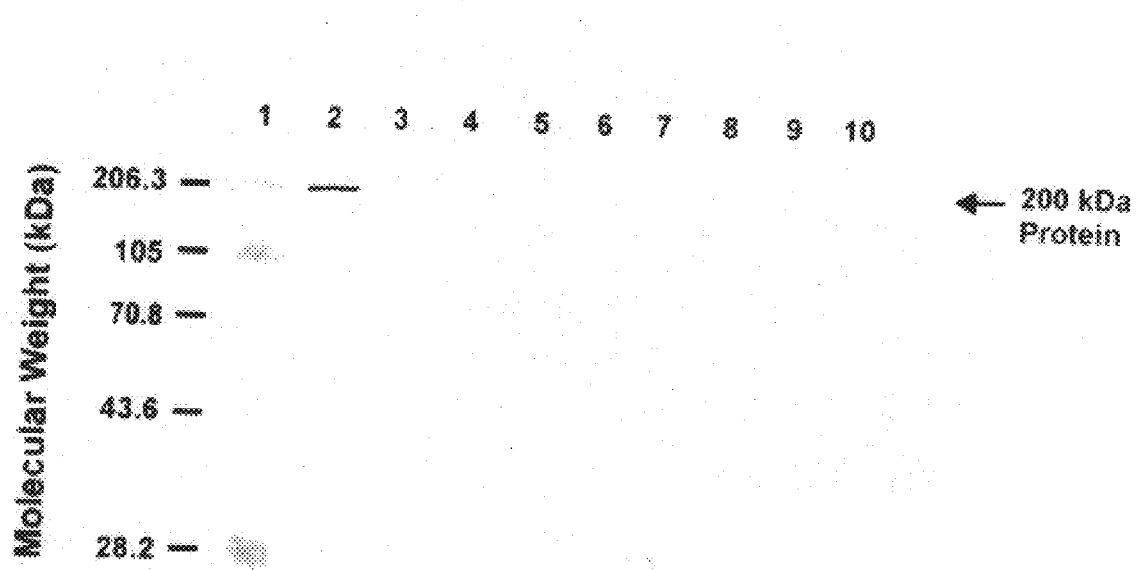
FIG. 7 shows the specific identification of *M. catarrhalis* expressing the about 200 kDa outer membrane protein by guinea pig anti-200 kDa specific antiserum in contrast to other bacteria. Identification of the lanes and bacteria appears below.

The results shown in FIG. 7 clearly show the usefulness of outer membrane-specific antisera as provided herein to distinguish between bacterial pathogens that produce diseases with similar clinical symptoms.

Thus, in accordance with another aspect of the present invention, there is provided a vaccine against Moraxella, comprising an immunogenically-effective amount of the outer membrane protein as provided herein and a physiologically-acceptable carrier therefor. The outer membrane protein provided herein also may be used as a carrier protein for hapten, polysaccharides or peptides to make a conjugate vaccine against antigenic determinants unrelated to the about 200 kDa outer membrane protein.

The about 200 kDa outer membrane protein provided herein is useful as a diagnostic reagent, as an antigen for the generation of anti-outer membrane protein antibodies, or as an antigen for vaccination against the diseases caused by species of Moraxella for detecting infection by Moraxella.

In additional embodiments of the present invention, the about 200 kDa outer membrane protein as provided herein may be used as a carrier molecule to prepare chimeric molecules and conjugate vaccines (including glycoconjugates) against pathogenic bacteria, including encapsulated bacteria. Thus, for example, glycoconjugates of the present invention may be used to confer protection against disease and infection caused by any bacteria having polysaccharide antigens including lipooligosaccharides (LOS) and polyribosylphosphate (PRP). Such bacterial pathogens may include, for example, *Haemophilus influenzae, Streptococcus pneumoniae, Escherichia coli, Neisseria meningitides, Salmonella typhi, Streptococcus mutants, Cryptococcus neoformans,* Klebsiella, *Staphylococcus aureus* and *Pseudomonas aeruginosa.* Particular antigens which can be conjugated to outer membrane protein and methods to achieve such conjugations are described in published PCT application WO 94/12641, assigned to the assignee hereof and the disclosure of which is hereby incorporated by reference thereto.

In another embodiment, the carrier function of the outer membrane protein may be used, for example, to induce immunity toward abnormal polysaccharides of tumor cells, or to produce anti-tumor antibodies that can be conjugated to chemotherapeutic or bioactive agents.

It is clearly apparent to one skilled in the art, that the various embodiments of the present invention have many applications in the fields of vaccination, diagnosis, treatment of Moraxella infections, and in the generation of immunological reagents. A further non-limiting discussion of such uses is further presented below.

1. Vaccine Preparation and Use

Immunogenic compositions, suitable to be used as vaccines, may be prepared from the about 200 kDa outer membrane protein as disclosed herein, which may be purified from the bacteria or which may be produced recombinantly, as well as immunological fragments thereof. The vaccine elicits an immune response in a subject which produces antibodies, including anti-200 kDa outer membrane protein antibodies and antibodies that are opsonizing or bactericidal. Should the vaccinated subject be challenged by Moraxella or other bacteria that produce proteins capable of producing antibodies that specifically recognize 200 kDa outer membrane protein, the antibodies bind to and inactivate the bacterium. Furthermore, opsonizing or bactericidal anti-200 kDa outer membrane protein antibodies may also provide protection by alternative mechanisms.

Immunogenic compositions including vaccines may be prepared as injectables, as liquid solutions or emulsions. The about 200 kDa outer membrane protein may be mixed with pharmaceutically acceptable excipients which are compatible with the about 200 kDa outer membrane protein. Such excipients may include, water, saline, dextrose, glycerol, ethanol, and combinations thereof. The immunogenic compositions and vaccines may further contain auxiliary substances, such as wetting or emulsifying agents, pH buffering agents, or adjuvants to enhance the effectiveness thereof. Immunogenic compositions and vaccines may be administered parenterally, by injection subcutaneously or intramuscularly. Alternatively, the immunogenic compositions formed according to the present invention, may be formulated and delivered in a manner to evoke an immune response at mucosal surfaces. Thus, the immunogenic composition may be administered to mucosal surfaces by, for example, the nasal or oral (intragastric) routes. Alternatively, other modes of administration including suppositories and oral formulations may be desirable. For suppositories, binders and carriers may include, for example, polyalkalene glycols or triglycerides. Oral formulations may include normally employed incipients such as, for example, pharmaceutical grades of saccharine, cellulose and magnesium carbonate. These compositions can take the form of solutions, suspensions, tablets, pills, capsules, sustained release formulations or powders and contain about 1 to 95% of the about 200 kDa outer membrane protein. The immunogenic preparations and vaccines are administered in a manner compatible with the dosage formulation, and in such amount as will be therapeutically effective, protective and immunogenic. The quantity to be administered depends on the subject to be treated, including, for example, the capacity of the individual's immune system to synthesize antibodies, and if needed, to produce a cell-mediated immune response. Precise amounts of active ingredient required to be administered depend on the judgment of the practitioner. However, suitable dosage ranges are readily determinable by one skilled in the art and may be of the order of micrograms of the about 200 kDa outer membrane protein. Suitable regimes for initial administration and booster doses are also variable, but may include an initial administration followed by subsequent administrations. The dosage may also depend on the route of administration and will vary according to the size of the host.

The concentration of the about 200 kDa outer membrane antigen in an immunogenic composition according to the invention is in general about 1 to 95%. A vaccine which contains antigenic material of only one pathogen is a monovalent vaccine. Vaccines which contain antigenic material of several pathogens are combined vaccines and also belong to the present invention. Such combined vaccines contain, for example, material from various pathogens or from various strains of the same pathogen, or from combinations of various pathogens.

Immunogenicity can be significantly improved if the antigens are co-administered with adjuvants, commonly used as 0.05 to 0.1 percent solution in phosphate-buffered saline. Adjuvants enhance the immunogenicity of an antigen but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses.

Immunostimulatory agents or adjuvants have been used for many years to improve the host immune responses to, for example, vaccines. Intrinsic adjuvants, such as lipopolysaccharides, normally are the components of the killed or attenuated bacteria used as vaccines. Extrinsic adjuvants are immunomodulators which are typically non-covalently linked to antigens and are formulated to enhance the host immune responses. Thus, adjuvants have been identified that enhance the immune response to antigens delivered parenterally. Some of these adjuvants are toxic, however, and can cause undesirable side-effects, making them unsuitable for use in humans and many animals. Indeed, only aluminum hydroxide and aluminum phosphate (collectively commonly referred to as alum) are routinely used as adjuvants in human and veterinary vaccines. The efficacy of alum in increasing antibody responses to diphtheria and tetanus toxoids is well established and, more recently, a HBsAg vaccine has been adjuvanted with alum. While the usefulness of alum is well established for some applications, it has limitations. For example, alum is ineffective for influenza vaccination and inconsistently elicits a cell mediated immune response.

A wide range of extrinsic adjuvants can provoke potent immune responses to antigens. These include saponins complexed to membrane protein antigens (immune stimulating complexes), pluronic polymers with mineral oil, killed mycobacteria in mineral oil, Freund's complete adjuvant, bacterial products, such as muramyl dipeptide (MDP) and lipopolysaccharide (LPS), as well as lipid A, and liposomes.

To efficiently induce humoral immune responses (HIR) and cell-mediated immunity (CMI), immunogens are emulsified in adjuvants. Many adjuvants are toxic, inducing granulomas, acute and chronic inflammations (Freund's complete adjuvant) FCA, cytolysis (saponins and Pluronic polymers) and pyrogenicity, arthritis and anterior uveitis (LPS and MDP). Although FCA is an excellent adjuvant and widely used in research, it is not licensed for use in human or veterinary vaccines because of its toxicity.

Desirable characteristics of ideal adjuvants include:

(1) lack of toxicity;

(2) ability to stimulate a long-lasting immune response;

(3) simplicity of manufacture and stability in long-term storage;

(4) ability to elicit both CMI and HIR to antigens administered by various routes, if required;

(5) synergy with other adjuvants;

(6) capability of selectively interacting with populations of antigen presenting cells (APC);

(7) ability to specifically elicit appropriate $T_H1$ or $T_H2$ cell-specific immune responses; and (8) ability to selectively increase appropriate antibody isotype levels (for example, IgA) against antigens. U.S. Pat. No. 4,855,283 granted to Lockhoff et al on Aug. 8, 1989 which is incorporated herein by reference thereto, teaches glycolipid analogues including N-glycosylamides, N-glycosylureas and N-glycosylcarbamates, each of which is substituted in the sugar residue by an amino acid, as immunomodulators or adjuvants. Thus, Lockhoff et al. (U.S. Pat. No. 4,855,283 and ref. 27) reported that N-glycolipid analogs displaying structural similarities to the naturally-occurring glycolipids, such as glycosphingolipids and glycoglycerolipids, are capable of eliciting strong immune responses in both herpes simplex virus vaccine and pseudorabies virus vaccine. Some glycolipids have been synthesized from long chain-alkylamines and fatty acids that are linked directly with the sugars through the anomeric carbon atom, to mimic the functions of the naturally occurring lipid residues.

U.S. Pat. No. 4,258,029 granted to Moloney, assigned to the assignee hereof and incorporated herein by reference thereto, teaches that octadecyl tyrosine hydrochloride (OTH) functioned as an adjuvant when complexed with tetanus toxoid and formalin inactivated type I, II and III poliomyelitis virus vaccine. Also, Nixon-George et al. (ref. 24), reported that octadecyl esters of aromatic amino acids complexed with a recombinant hepatitis B surface antigen, enhanced the host immune responses against hepatitis B virus.

Lipidation of synthetic peptides has also been used to increase their immunogenicity. Thus, Wiesmuller (ref. 25) describes a peptide with a sequence homologous to a foot-and-mouth disease viral protein coupled to an adjuvant tripalmityl-S-glyceryl-cysteinylserylserine, being a synthetic analogue of the N-terminal part of the lipoprotein from Gram negative bacteria. Furthermore, Deres et al. (ref. 26) reported in vivo priming of virus-specific cytotoxic T lymphocytes with synthetic lipopeptide vaccine which comprised of modified synthetic peptides derived from influenza virus nucleoprotein by linkage to a lipopeptide, N-palmityl-S-[2,3-bis(palmitylxy)-(2RS)-propyl-[R]-cysteine (TPC).

2. Immunoassays

The about 200 kDa outer membrane protein of the present invention is useful as an immunogen for the generation of anti-200 kDa outer membrane protein antibodies, as an antigen in immunoassays including enzyme-linked immunosorbent assays (ELISA), RIAs and other non-enzyme linked antibody binding assays or procedures known in the art for the detection of anti-bacterial, anti-Moraxella, and anti-200 kDa outer membrane protein antibodies. In ELISA assays, the about 200 kDa outer membrane protein is immobilized onto a selected surface, for example, a surface capable of binding proteins such as the wells of a polystyrene microtiter plate. After washing to remove incompletely adsorbed about 200 kDa outer membrane protein, a nonspecific protein such as a solution of bovine serum albumin (BSA) that is known to be antigenically neutral with regard to the test sample may be bound to the selected surface. This allows for blocking of nonspecific adsorption sites on the immobilizing surface and thus reduces the background caused by nonspecific bindings of antisera onto the surface.

The immobilizing surface is then contacted with a sample, such as clinical or biological materials, to be tested in a manner conducive to immune complex (antigen/antibody) formation. This may include diluting the sample with diluents, such as solutions of BSA, bovine gamma globulin (BGG) and/or phosphate buffered saline (PBS)/Tween. The sample is then allowed to incubate for from 2 to 4 hours, at temperatures such as of the order of about 20° to 37° C. Following incubation, the sample-contacted surface is washed to remove non-immunocomplexed material. The washing procedure may include washing with a solution, such as PBS/Tween or a borate buffer. Following formation of specific immunocomplexes between the test sample and the bound about 200 kDa outer membrane protein, and subsequent washing, the occurrence, and even amount, of immunocomplex formation may be determined by subjecting the immunocomplex to a second antibody having specificity for the first antibody. If the test sample is of human origin, the second antibody is an antibody having specificity for human immunoglobulins and in general IgG. To provide detecting means, the second antibody may have an associated activity such as an enzymatic activity that will generate, for example, a colour development upon incubating with an appropriate chromogenic substrate. Quantification may then be achieved by measuring the degree of colour generation using, for example, a visible spectrophotometer.

BIOLOGICAL MATERIALS

Certain plasmids that contain portions of the gene having the open reading frame of the gene coding for the about 200 kDa outer membrane protein of *M. catarrhalis* strain 4223 that are described and referred to herein have been deposited with the America Type Culture Collection (ATCC) located at 12301 Parklawn Drive, Rockville, Md., 20852, U.S.A., pursuant to the Budapest Treaty and prior to the filing of this application. The identification of the respective portions of the gene and their molecular size are contained in FIG. 5.

Samples of the deposited plasmids will become available to the public upon grant of a patent based upon this United States patent application. The invention described and claimed herein is not to be limited in scope by plasmids deposited, since the deposited embodiment is intended only as an illustration of the invention. Any equivalent or similar plasmids that encode similar or equivalent antigens as described in this application are within the scope of the invention.

| Plasmid | ATCC Designation | Date Deposited |
|---------|------------------|----------------|
| pKS47   | 97,111           | April 7, 1995  |
| pKS5    | 97,110           | April 7, 1995  |
| pKS9    | 97,114           | April 18, 1995 |

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations.

Methods of molecular genetics, protein biochemistry, and immunology used but not explicitly described in this disclosure and these Examples are amply reported in the scientific literature and are well within the ability of those skilled in the art.

EXAMPLE 1

This Example illustrates the generation of a non-clumping strain (RH408) of *M. catarrhalis*.

*M. catarrhalis* strain 4223, a clumping strain (a common property of Moraxella strains), was inoculated into several flasks containing 20 mL of brain heat infusion (BHI) broth, and the cultures were incubated with shaking (170 rpm) overnight at 37° C. Five mL of each overnight culture were transferred to five individual 1-mL tubes, and were left sitting undisturbed at room temperature for 3 to 8 hours, to allow bacteria to sediment. One hundred $\mu$L of the cleared upper phase of each culture medium were used to inoculate 25 mL of BHI broth and cultures were incubated overnight at 37° C., as described above. This passaging was repeated six times, using 25 $\mu$L of cleared medium to inoculate 25 mL of BHI for each overnight culture. Non-clumping bacterial cultures were identified by measuring the absorbency $A_{578}$ at intervals over a 3 hour time period, in order to compare the sedimentation rates of the passaged strains to that of the original *M. catarrhalis* strain 4223 culture. Non-clumping mutants, including *M. catarrhalis* RH408, did not aggregate during the three hour time period. On BHI agar plates, strain RH408 had a colony morphology typical for all non-clumping strains. Strain RH408 was previously deposited at the ATCC under the Budapest Treaty on Dec. 13, 1994 with Accession No. 55637.

EXAMPLE 2

This Example illustrates the identification of the above 200 kDa outer membrane protein of *Moraxella catarrhalis*.

*M. catarrhalis* strains 4223, RH408, 5191, 8185, M2, M5, ATCC 25240, 3, 56, 135, 585 were grown in brain heart infusion (BHI) broth. The culture was incubated overnight with aeration at 37° C.

*M. catarrhalis* cells were sonicated and the total protein was determined using the BCA assay system (Pierce, Rockford, Ill.). Ten $\mu$g of total protein were mixed with the SDS-PAGE sample buffer containing 0.3M Tris-HCl (pH 8.0), 50% glycerol, 10% SDS, 20% $\alpha$-mercaptoethanol and 0.01% bromophenol blue, boiled for 5 minutes and loaded on each lane of SDS-PAGE gel (0.75 mm thick, 7.5% acrylamide). The gels were run at 200 V for 1 hour. Proteins were visualized by staining gels with a solution containing 0.13% Commassie brilliant blue R, 10% acetic acid and 45% methanol. Excess stain was removed with a destaining solution of 5% ethanol and 7.5% acetic acid.

The various Moraxella proteins separated by this procedure are shown in FIGS. 1A and 1B. The *M. catarrhalis* strains tested were as follows:

| Lane | Bacterial Strain | Source |
|------|------------------|--------|
| FIG. 1A | | |
| 1. | Molecular Weight Standards | |
| 2. | *E. coli* | |
| 3. | No sample | |
| 4. | *M. catarrhalis* 4223 | middle ear fluid |
| 5. | *M. catarrhalis* RH408 | non-clumping variant of 4223 |

-continued

| Lane | Bacterial Strain | Source |
|---|---|---|
| 6. | M. catarrhalis 5191 | middle ear fluid |
| 7. | M. catarrhalis 8185 | nasopharynx |
| 8. | M. catarrhalis M2 | sputum |
| 9. | M. catarrhalis M5 | sputum |
| 10. | M. catarrhalis 25240 | ATCC 25240 |
| FIG. 1B | | |
| 1. | E. coli | |
| 2. | No sample | |
| 3. | Molecular Weight Size Markers | |
| 4. | M. catarrhalis 4223 | middle ear fluid |
| 5. | M. catarrhalis RH408 | non-clumping variant of 4223 |
| 6. | M. catarrhalis 3 | sputum |
| 7. | M. catarrhalis 56 | sputum |
| 8. | M. catarrhalis 135 | middle ear fluid |
| 9. | M. catarrhalis 585 | Blood |

The about 200 kDa outer membrane protein was clearly seen in all otitis media strains (M. catarrhalis 4223, 5191, 135), one isolate from nasopharynx (8185), and in one isolate from sputum (M2). However, the about 200 kDa protein was not detected in three isolates from sputum (3, 56 and M5) and in one strain with unknown origin (ATCC 25240). A very narrow band was found in an isolate from blood of a bacteremia patient (585) and this band was recognized by an anti-200 kDa specific guinea pig serum on an immunoblot. Strain RH408 is a non-clumping spontaneous mutant isolated from strain 4223 (see Example 1) and was found to not express the about 200 kDa protein.

EXAMPLE 3

This Example illustrates the detection of antibodies specific for the about 200 kDa outer membrane protein in a serum obtained from a convalescent patient having recovered from otitis media due to M. catarrhalis.

After separation by SDS-PAGE, bacterial proteins were transferred from acrylamide gels to prepared PVDF (polyvinylidene-fluoride; Millipore) membranes at a constant voltage of 70 V for 1.5 h in a buffer system consisting of 3 g Tris, 14,4 g glycine and 200 ml methanol per liter at 4° C. Membranes with transferred proteins were blocked with Blocking Reagent (from Boehringer Mannheim) diluted in TBS (0.1M Tris, 0.15M Nacl) at room temperature for 30 min. Blots were exposed to convalescent antiserum diluted 1:500 in Blocking Reagent/TBS with 0.1% Tween 20 for 2 hours at room temperature. This patient had otitis media and the M. catarrhalis strain isolated from the patient's ear fluid was M. catarrhalis CJ7. Blots were then washed 2 times in Blocking Reagent/TBS with Tween at 15 min per wash. The reporter conjugate, horseradish peroxidase (HRP) conjugated to protein G, was diluted 1:4000 with Blocking Reagent/TBS with Tween and used to immerse the washed membranes for 30 min at room temperature. Blots were washed twice as above, followed by a TBS wash. Bound antibodies were detected using the Lumi-Glo (Kirkegaard and Perry) chemiluminescent detection system as described by the manufacturer. Treated blots were exposed to X-ray film. Antibodies were detected in this convalescent serum that reacted with the about 200 kDa outer membrane protein of M. catarrhalis CJ7. These results indicate that the about 200 kDa outer membrane protein is an immunogenic protein of M. catarrhalis to which an immune response is elicited during a natural infection by M. catarrhalis.

EXAMPLE 4

This Example illustrates the isolation and purification of the about 200 kDa outer membrane protein.

M. catarrhalis 4223 cells were harvested by centrifugation at 2,000 rpm for 10 min and frozen. The frozen cells were thawed, resuspended in 20 mM sodium phosphate buffer (pH 7.2) and sonicated until the cells were disrupted. The frozen-thawed cells were also lysed in 20 mM Tris buffer (pH 8) containing 4% SDS and 0.2 mM EDTA by boiling for 5 min to produce a cell lysate. The cell sonicates and cell lysates were suspended in a SDS-polyacrylamide gel electrophoresis (SDS-PAGE) sample buffer, boiled for 5 min and separated by SDS-PAGE on a gel (1.5 mm thick, 7.5% acrylamide). The estimated position of about 200 kDa protein on the gel was cut out and the protein extracted from the gel by electroelution using the same buffer as the SDS-PAGE running buffer. The isolated about 200 kDa outer membrane protein was shown to be a homogeneous, single band by SDS-PAGE as seen in FIG. 3. The samples analyzed in FIG. 3 are as follows:

| Lane | Sample |
|---|---|
| 1. | Molecular Weight Size Markers |
| 2. | Isolated and purified 200 kDa outer membrane protein |

The isolated and purified 200 kDa outer membrane protein of M. catarrhalis shown in FIG. 3 has a purity of at least 70%. Purified about 200 kDa outer membrane protein preparations of at least 95% could be readily achieved.

When gels were run longer, they showed heterogeneity in the apparent molecular masses of the about 200 kDa outer membrane protein in different strains of M. catarrhalis (FIG. 2). In FIG. 2 the strains analyzed were as follows:

| Lane | Strain | Source |
|---|---|---|
| 1. | Molecular Weight Size Markers | |
| 2. | M. calarrhalis H04 | middle ear fluid |
| 3. | M. catarrhalis H12 | middle ear fluid |
| 4. | M. calarrhalis PO34 | middle ear fluid |
| 5. | M. catarrhalis PO51 | middle ear fluid |
| 6. | M. catarrhalis E-07 | middle ear fluid |
| 7. | M. catarrhalis E-22 | middle ear fluid |
| 8. | M. catarrhalis E-23 | middle ear fluid |
| 9. | M. catarrhalis RH 4223 | middle ear fluid |
| 10. | M. catarrhalis RH 408 | Non-clumping variant of 4223 |

The strain H12 (lane 3) was a natural isolate from middle ear fluid, but did not produce the about 200 kDa protein.

There may be at least three different sizes of protein in the about 200 kDa range. However, antibodies raised against the about 200 kDa outer membrane protein from one strain of M. catarrhalis (4223) did recognize all about 200 kDa proteins tested, present in different strains of M. catarrhalis. It is possible, however, that in particular immunogenic compositions, for example, as a vaccine and in particular diagnostic embodiments, that the about 200 kDa outer membrane protein from a variety of M. catarrhalis isolates (including immunogenically diverse isolates) may be required.

EXAMPLE 5

This Example illustrates the immunization of guinea pigs with purified about 200 kDa protein from M. Catarrhalis.

Approximately 30 to 40 μg of the about 200 kDa protein, which was isolated from *M. catarrhalis* strain 4223 by electroelution, were mixed with Freund's complete adjuvant (FCA) and was subcutaneously injected into guinea pigs. After two weeks, the animals were boosted with about the same amount of the about 200 kDa protein in incomplete Freund's adjuvant (IFA). Two weeks later, blood was collected from the guinea pigs and antisera were obtained.

One antiserum was examined on Western blot for its reactivity with the about 200 kDa protein present in 54 different strains of *M. catarrhalis*, which were isolated in different geographical locations throughout the world (Canada, U.S. and Finland) (see Table 1 below). The about 200 kDa protein band was clearly recognized by the antiserum in all strains, in which the presence of the about 200 kDa protein band was detected on SDS-PAGE gels stained with Coomassie Blue. These results indicate that common epitopes of the about 200 kDa protein were conserved in all *M. catarrhalis* strains, which possessed this protein. As stated earlier, this protein is not present in all *M. catarrhalis* strains, but almost all strains, which were isolated from middle ear fluids from otitis media patients, did possess this protein (Table 1).

EXAMPLE 6

This Example illustrates the specific recognition of *M. catarrhalis* strain 4223 with anti-200 kDa protein guinea pig serum by ELISA assay (see Table 2 below).

*M. catarrhalis* strains 4223, RH408 (200 kDa negative mutant) and H-12 were cultured in 60 mL BHI broth overnight. *E. coli* strain BL21 (DE3) was cultured in 60 mL Luria-Brtani (LB) broth overnight. The cultures were split into three tubes and centrifuged. *M. catarrhalis* strain 4223 was centrifuged at 1,500 rpm for 10 minutes, H-12 at 2,000 rpm for 10 minutes, and RH408 and *E. coli* BL21 (DE3) at 3,000 rpm for 15 minutes. The pellet in one tube was suspended in 20 ml of Dulbecco's phosphate buffered saline (D-PBS) and diluted to 1/500 with coating buffer (0.05M carbonate/bicarbonate buffer) pH 9.6. One hundred μL of the bacteria solution was distributed in each well and incubated for 1 hour at room temperature. one hundred μL of 0.2% glutaraldehyde was added to each well and incubated at room temperature for 10 minutes to fix the cells on the well. The wells were washed with PBS containing 0.1% Tween 20 and 0.1% BSA (washing buffer), and then blocked with PBS containing 0.1% BSA for 30 minutes at room temperature. After washing 5 times for 10 seconds with the washing buffer, serial dilutions of guinea pig antiserum with the washing buffer were added to wells and incubated at room temperature for 60 minutes. After washing, goat anti-guinea pig IgG conjugated with horseradish peroxidase was added to each well at the dilution of 1/20,000. After incubation at room temperature for 60 minutes, the wells were washed and then color reaction was developed using 3,3-5,5-tetramethylbenzidene (TMB) and hydrogen peroxide.

The ELISA plate wells were also coated with sonicates containing 10 μg/mL of total proteins in the coating buffer, blocked without the fixation process and then assayed as described above.

The results shown in Table 2 indicate that the 200 kDa outer membrane protein specific guinea pig antiserum specifically recognizes strains of *M. catarrhalis* which produce the about 200 kDa protein. The ability of the antiserum to recognize whole cells indicates that the protein is present on the surface of the bacterial cells.

EXAMPLE 7

This Example describes the determination of an internal amino acid sequence of the 200 kDa outer membrane protein.

The about 200 kDa outer membrane protein was isolated from *M. catarrhalis* 4223 as described above. The protein was subjected to CNBr degradation, the proteolytic digests subjected to SDS-PAGE and transferred onto PVDF membrane. A peptide band migrating at a position corresponding to approximately 40 kDa was cut out from the membrane and its N-terminal amino acid sequence was determined. In another experiment, the CNBr degradation products of the about 200 kDa protein were subjected to a direct determination of N-terminal amino acid sequencing without separating by SDS-PAGE. Both analyses gave an identical, N-terminal sequence of 20 amino acids with one unidentified amino acid at the 17th position. The internal sequence of the 200 kDa outer membrane protein was:

NH$_2$-Asn-Val-Lys-Ser-Val-Ile-Asn-Lys-Glu-Gln-Val-Asn-Asp-Ala-Asn-Lys-X-Gln-Gly-Ile (SEQ ID No: 2).

EXAMPLE 8

This Example describes the immunization of guinea pigs with a peptide corresponding to an internal fragment of the about 200 kDa outer membrane protein and the analysis of the antiserum generated.

Based upon the determination of the amino acid sequence of an internal fragment of the about 200 kDa outer membrane protein, a 16 amino acid long peptide of sequence:

NH$_2$-Asn-Val-Lys-Ser-Val-Ile-Asn-Lys-Glu-Gln-Val-Asn-Asp-Ala-Asn-Lys (SEQ ID No: 3)

was synthesized by standard procedure. This 16-mer peptide was conjugated to KLH using Imject Maleimide Activated KLH (Pierce, Rockford, Ill.) and approximately 500 μg of the conjugate was injected into guinea pigs using the same immunization and boosting schedule as described above. The guinea pig serum raised against the 16-mer internal amino acid sequence (SEQ ID No: 3) was examined by immunoblot analysis and found to specifically recognize 200 kDa outer membrane protein in cell sonicates of *M. catarrhalis* 4223. The results are shown in FIG. 4 and indicate that the anti-peptide guinea pig antiserum specifically recognizes the 200 kDa protein of *M. catarrhalis* 4223. The samples analyzed in FIG. 4 were as follows:

| Lane | Sample | Antiserum |
|---|---|---|
| 1. | Molecular Weight Markers | |
| 2. | Purified 200 kDa outer membrane protein | Anti-200 kDa protein |
| 3. | *M. catarrhalis cell* sonicate | Anti-peptide 1:500 |
| 4. | *M. catarrhalis cell* sonicate | Anti-peptide 1:100 |
| 5. | *M. catarrhalis cell* sonicate | Anti-peptide 1:500 |
| 6. | *M. catarrhalis cell* sonicate | Pre-immune serum |

The results obtained confirm that the peptide corresponding to SEQ ID Nos: 2 and 3 are derived from the 200 kDa outer membrane protein.

EXAMPLE 9

This Example describes the preparation of a *M. catarrhalis* library.

Chromosomal DNA was isolated as follows:

*M. catarrhalis* cell pellet was resuspended in 20 mL Tris-EDTA (TE) buffer, pH 7.5. Pronase (final concentration 500 μg/mL) and SDS (final concentration 1%) were added and the suspension was incubated in a 37° C. water bath for 2 hours. DNA was isolated by sequential extractions with phenol (1 time), phenol-chloroform (1:1, 2 times), and chloroform-isoamyl alcohol (24:1, 1 time). Extracted DNA was dialyzed against 1M NaCl at 4° C. for 4 hours. This was followed by dialysis against TE buffer, pH 7.5, at 4° C. for 48 hours (3 buffer changes). DNA was ethanol precipitated from the dialysate. Large size DNA was collected by spooling on a glass rod. Air dried DNA was dissolved in 3 mL water. Small scale Sau3A (New England BioLabs) restriction digests of chromosomal DNA (final volume 10 µl) were done to establish conditions required to obtain maximal amounts of chromosomal DNA with a size range of 15–23 kb. Large scale digests were prepared once the optimal digestion conditions were defined. The large scale digests consisted of 50 µl chromosomal DNA (290 µg/mL), 33 µL water, 10 µL Sau3A buffer (New England BioLabs), 1 µL BSA (10 mg/ml, New England BioLabs) and 6.3 µL Sau3A (0.04 U/µL), and were incubated at 37° C. for 15 minutes. Reactions were stopped with the addition of 10 µL 10×loading buffer (100 mM Tris-HCl pH 8, 10 mM EDTA, 0.1% bromophenol blue, 50% glycerol). Digested DNA was applied to 0.5% agarose gels (prepared in Tris-acetate-EDTA (TAE)) and separated according to size at 50 V for 6 hours. The region of the gel encompassing DNA of size 15–23 kb was cut from the gel and placed in dialysis tubing (BRL) with 3 mL TAE. DNA was electroeluted from the gel slice overnight at a field strength of 1 V/cm. Electroeluted DNA in TAE was extracted once with phenol, once with phenol-chloroform (1:1), and finally precipitated with ethanol. The dried DNA pellet was dissolved in 5 µL water. Size-fractionated chromosomal DNA was ligated with BamHI cut EMBL3 arms (Promega) using T4 DNA ligase in a final volume of 9 µL. The entire ligation reaction was packaged into phage λ using a commercially purchased packaging kit following the manufacturer's (Amersham) protocol.

The packaged DNA library was amplified on solid medium. This was accomplished by incubating 0.1 ml E. coli strain NM539 plating cells (cells suspended in 10 mM MgSO$_4$) with 15–25 µL of the packaged DNA library at 37° C. for 15 minutes. Bacteria with adsorbed phage were plated onto BBL plates (10 g BBL trypticase peptone, 5 g NaCl and 15 g agar per liter) using 3 mL of BBL top-agarose (same as BBL plates except agar replaced with 0.6% agarose) and plates were incubated overnight at 37° C. Phage were eluted from the top-agarose by adding 3 mL SM buffer (50 mM Tris-HCl, pH 7.5, 8 mM MgSO$_4$, 100 mM NaCl, 0.01% gelatin) to the plates and leaving them at 4° C. for 7 hours. SM buffer containing phage was collected from the plates, transferred to a screwcap tube and stored at 4° C. over chloroform.

EXAMPLE 10

This Example describes the cloning on a gene encoding the M. catarrhalis 200 kDa outer membrane protein.

The M. catarrhalis genomic library in phage lambda EMBL3 was screened using an anti-200 kDa protein guinea pig antiserum. A lambda phage clone 8II (FIG. 5), which expressed as about 200 kDa protein, was confirmed by immunoblotting of the phage lysate using the about 200 kDa outer membrane-specific antiserum.

Plate lysate cultures of this recombinant phage were prepared. The DNA was extracted from the plate lysates using a Wizard Lambda Preps DNA Purification System (Promega Corp, Madison, Wis.) according to the manufacturer's instructions. This phage clone carried a DNA insert of about 16 kb in size (the restriction map for which is in FIG. 5). The phage DNA was digested with a mixture of two restriction enzymes, SalI and XhoI, and separated by agarose gel electrophoresis. Two DNA bands, approximately 5 kb and 11 kb in size, respectively, were cut out from the gel and extracted using a Geneclean kit (BIO 101 Inc., LaJolla, Calif.) according to a manufacturer's instruction.

The smaller 5 kb fragment was ligated into a plasmid vector, pBluescript II SK +/- (Stratagene Cloning Systems, LaJolla, Calif.), which was previously digested with SalI and XhoI, to produce plasmid pKS5. The larger 11 kb fragment was ligated into a plasmid vector, pSP72 (Promega Corp., Madison, Wis.), to produce plasmid pKS9.

Both ligated plasmids were used to transform E. coli, strain DH5α.

The lambda phage DNA was also digested with a mixture of XhoI and KpnI and the approximately 1.2 kb fragment was isolated after agarose gel separation as described above. This 1.2 kb fragment was ligated into a plasmid vector, pGEM-7Zf(+) (Promega Corp., Madison, Wis.), to produce plasmid pKS47. Restriction maps of the lambda and plasmid clones are shown in FIG. 5.

EXAMPLE 11

This Example describes the sequencing of the gene having an open reading frame of the gene coding for the about 200 kDa outer membrane protein of M. catarrhalis.

The gene encoding the about 200 kDa outer membrane protein was sequenced by an Applied Biosystems sequencer. The one strand of the insert in the plasmid pKS5, was sequenced after construction of a nested set of deletions using a Erase-a-Base system (Promega Corp., Madison, Wis.). The plasmid pKS5 was first digested with XhoI and KpnI, treated with exonuclease III to generate a nested set of deletions in the insert and then recircularized according to the manufacturer's instructions. E. coli DH5α was transformed with a series of plasmids with deletions generated in this way. Plasmids were isolated from the transformants using a Quiagen midi plasmid isolation kit (Qiagen) and the size of plasmids examined by agarose gel electrophoresis after restriction enzyme digestion. The inserts of the plasmids with deletions were sequenced using a bacteriophage T7 promoter sequence as a primer.

Based upon the sequence, nucleotide primers were synthesized. Using the synthetic nucleotide primers, sequence gaps, which were not sequenced by the Erase-a Base system, were determined.

The sequence of the insert in plasmid pKS47 was determined from both ends using synthetic nucleotide primers. The nucleotide sequence of the gene has an open reading frame of the gene coding for the about 200 kDa outer membrane protein of M. catarrhalis as shown in FIG. 6 (SEQ ID No: 1). This sequence included a nucleotide sequence:

5'-AATGTCAAATCAGTCATTAACAAAGAACAA-
GTAAATGATGCCAATAAAAAGCAAGGCATC-3'
(SEQ ID No: 4)

which encodes the internal amino acid sequence of the about 200 kDa outer membrane protein (SEQ ID No: 2) determined above. This result confirms that the cloned gene has an open reading frame of the gene coding for the about 200 kDa outer membrane protein of M. catarrhalis.

SUMMARY OF THE DISCLOSURE

In summary of the disclosure, the present invention provides an isolated and purified outer membrane protein of a Moraxella strain, particularly M. catarrhalis, having a molecular weight of about 200 kDa as well as isolated and purified DNA molecules encoding the outer membrane protein. The invention also provides peptides corresponding to portions of the outer membrane protein. The protein, DNA sequences, recombinant proteins derived therefrom and peptides are useful for diagnosis, immunization and the generation of diagnostic and immunological reagents. Modifications are possible within the scope of this invention.

TABLE I

Presence of about 200 kDa outer membrane protein in various isolates of *Moraxella catarrhalis*

| Type of Clinical Isolate | Number of isolates Examined | Number of isolates[1] containing the 200 kDa outer membrane protein |
|---|---|---|
| Otitis Media | 37 | 36 |
| Sputum/Expectoration/Bronchial Secretion | 13 | 6 |
| Blood | 2 | 2 |
| Nasopharynx | 1 | 1 |
| Unknown | 1 | 0 |

[1]The presence of the about 200 kDa outer membrane protein was determined by immunoblot analysis using a monospecific guinea pig anti-200 kDa protein antiserum.

TABLE II

Detection of about 200 kDa outer membrane protein of *M. catarrhalis* by the monospecific anti-200 kDa outer membrane guinea pig antiserum

| Strain | Sample | Reciprocal Reactive Titre |
|---|---|---|
| 4223 | Whole cells not fixed | 800 |
| RH408 | Whole cells not fixed | <200 |
| H12 | Whole cells not fixed | <200 |
| *E. coli* BL21 | Whole cells not fixed | <200 |
| 4223 | | 3200 |
| RH408 | | 200 |
| H12 | | <200 |
| *E. coli* BL21 | | <200 |
| 4223 | Sonicate | 12,800 |
| RH408 | Sonicate | 800 |
| H12 | Sonicate | 800 |
| *E. coli* BL21 | Sonicate | 200 |

REFERENCES

1. Van Hare, G. F., P. A. Shurin, C. D. Marchant, N. A. Cartelli, C. E. Johnson, D. Fulton, S. Carlin, and C. H. Kim. Acute otitis media caused by *Branhamella catarrhalis*: biology and therapy. Rev. Infect. Dis. 9:16–27.
2. Chapman, A. J., D. M. Musher, S. Jonsson, J. E. Clarridge, and R. J. Wallace. 1985. Development of bactericidal antibody during *Branhamella catarrhalis* infection. J. Infect. Dis. 151:878–882.
3. Hager, H., A. Verghese, S. Alvarez, and S. L. Berk. 1987. *Branhamella catarrhalis* respiratory infections. Rev. Infect. Dis. 9:1140–1149.
4. McLeod, D. T., F. Ahmad, M. J. Croughan, and M. A. Calder. 1986. Bronchopulmonary infection due to *M. catarrhalis*. Clinical features and therapeutic response. Drugs 31(Suppl. 3):109–112.
5. Nicotra, B., M. Rivera, J. I. Luman, and R. J. Wallace. 1986. *Branhamella catarrhalis* as a lower respiratory tract pathogen in patients with chronic lung disease. Arch. Intern. Med. 146:890–893.
6. Ninane, G., J. Joly, and M. Kraytman. 1978. Bronchopulmonary infection due to *Branhamella catarrhalis* 11 cases assessed by transtracheal puncture. Br. Med. Jr. 1:276–278.
7. Srinivasan, G., M. J. Raff, W. C. Templeton, S. J. Givens, R. C. Graves, and J. C. Mel. 1981. *Branhamella catarrhalis* pneumonia. Report of two cases and review of the literature. Am.Rev. Respir. Dis. 123:553–555.
8. West, M., S. L. Berk, and J. K. Smith. 1982. *Branhamella catarrhalis* pneumonia. South. Med. J. 75:1021–1023.
9. Brorson, J-E., A. Axelsson, and S. E. Holm. 1976. Studies on *Branhamella catarrhalis* (*Neisseria catarrhalis*) with special reference to maxillary sinusitis. Scan. J. Infect. Dis. 8:151–155.
10. Evans, F. O., Jr., J. B. Sydnor, W. E. C. Moore, G. R. Moore, J. L. Manwaring, A. H. Brill, R. T. Jackson, S. Hanna, J. S. Skaar, L. V. Holdeman, G. S. Fitz-Hugh, M. A. Sande, and J. M. Gwaltney, Jr. 1975. Sinusitis of the maxillary antrum. N. Engl. J. Med. 293:735–739.
11. Tinkelman, D. G., and H. J. Silk. 1989. Clinical and bacteriologic features of chronic sinusitis in children. Am. J. Dis. Child. 143:938–942.
12. Wald, E. R., C. Byers, N. Guerra, M. Casselbrant, and D. Beste. 1989. Subacute sinusitis in children. J. Pediatr. 115:28–32.
13. Wald, E. R., G. J. Milmoe A. Bowen, J. Ledesma-Medina, N. Salamon$_1$ and C. D. Bluestone. 1981. Acute maxillary sinusitis in children. N. Engl. J. Med. 304:749–754.
14. Christensen, J. J., and B. Bruun. 1985. Bacteremia caused by a beta-lactamase producing strain of *Branhamella catarrhalis*. Acta.Pathol. Microbiol. Immunol. Scand. Sect.B 93:273–275.
15. Craig, D. B., and P. A. Wehrle. 1983. *Branhamella catarrhalis* septic arthritis. J. Rheumatol. 10:985–986.
16. Gray, L. D., R. E. Van Scoy, J. P. Anhalt, and P. K. W. Yu. 1989. Wound infection caused by *Branhamella catarrhalis*. J. Clin. Microbiol. 27:818–820.
17. Guthrie, R., K. Bakenhaster, R. Nelson, and R. Woskobnick. 1988. *Branhamella catarrhalis* sepsis: a case report and review of the literature. J. Infect. Dis. 158:907–908.
18. Hiroshi, S., E. J. Anaissie, N. Khardori, and G. P. Bodey. 1988. *Branhamella catarrhalis* septicemia in patients with leukemia. Cancer 61:2315–2317.
19. O'Neill, J. H., and P. W. Mathieson. 1987. Meningitis due to *Branhamella catarrhalis*. Aust. N.Z. J. Med. 17:241–242.
20. Murphy, T. F. 1989. The surface of *Branhamella catarrhalis*: a systematic approach to the surface antigens of an emerging pathogen. Pediatr. Infect. Dis. J. 8: S75–S77.
21. Klingman, K. L., and T. F. Murphy. 1994. Purification and characterization of a high-molecular-weight outer membrane protein of *Moraxella* (Branhamella) *catarrhalis*. Infect. Immun. 62:1150–1155.
22. Helminen, M. E., I. Maciver, J. L. Latimer, J. Klesney-Tait, L. D. Cope, M. Paris, G. H. McCracken, Jr., and E. J. Hansen. 1994. A large, antigenically conserved protein on the surface of *Moraxella catarrhalis* is a target for protective antibodies. J. Infect. Dis. 170:867–872.
23. Panezutti H., O. James, E. J. Hanson, Y. Choi, R. E. Harkness, M. H. Klein and P. Chong, 1993. Identification of surface-exposed B-cell epitopes recognized by *Haemophilus influenzae* type b P1 specific monoclonal antibodies. Infec. Immun. 61:1867–1872.
24. Nixon-George et al. (1990), J. Immunology 144:4798–4802.
25. Wiesmuller (1989), Vaccine 8:29–33.
26. Deres et al. (1989), Nature 342:561.
27. Lockhoff, O. Glycolipids as Immmunomodulators: Synthesis and Properties. 1991. Chem. Int. Ed. Engl. 30:1611–1620.

What we claim is:

1. An immunogenic composition, comprising at least one active component selected from the group consisting of:
   (A) an isolated and purified outer membrane protein of a strain of *Moraxella catarrhalis* having a molecular mass of about 200 kDa, as determined by SDS-PAGE; and
   (B) a peptide consisting of the amino acid sequence NH$_2$-Asn-Val-Lys-Ser-Val-Ile-Asn-Lys-Glu-Gln-Val-Asn-Asp-Ala-Asn-Lys-x-Gln-Gly-Ile (SEQ ID No: 2) or NH$_2$-Asn-Val-Lys-Ser-Val-Ile-Asn-Lys-Glu-Gln-Val-Asn-Asp-Ala-Asn-Lys (SEQ ID No: 3); and a pharmaceutically acceptable carrier therefor, said at least one active component producing an immune response when administered to a host.

2. The immunogenic composition of claim 1 formulated as a microparticle, capsule, ISCOM, or liposome preparation.

3. The immunogenic composition of claim 1 in combination with a targeting molecule for delivery to specific cells of the immune system or to mucosal surfaces.

4. The immunogenic composition of claim 1 further comprising at least one other immunogenic or immunostimulating material.

5. The immunogenic composition of claim 4 wherein the at least one other immunostimulating material is at least one adjuvant.

6. The immunogenic composition of claim 5 wherein the at least one adjuvant is selected from the group consisting of aluminum phosphate, aluminum hydroxide, QS21, Quil A, calcium phosphate, calcium hydroxide, zinc hydroxide, a glycolipid analog, an octodecyl ester of an amino acid, a muramyl dipeptide and a lipoprotein.

7. The immunogenic composition of claim 6 wherein the host is a primate.

8. The immunogenic composition of claim 7 wherein the primate is a human.

9. A method of generating an immune response in a host, comprising administering thereto an immuno-effective amount of the immunogenic omposition of claim 1.

10. The method of claim 9 wherein the immune response is a humoral or a cell-mediated immune response.

11. A method of producing an isolated and purified outer membrane protein of a strain of *Moraxella catarrhalis* having a molecular mass of about 200 kDa, as determined by SDS-PAGE, comprising the steps of:
   (a) providing a cell mass of the *Moraxella catarrhalis* strain;
   (b) disrupting the cell mass to provide a cell lysate;
   (c) fractionating the cell lysate to provide a fraction containing the outer membrane protein substantially free from other cell lysate components, and
   (d) recovering said outer membrane protein.

12. The method of claim 11 wherein said *Moraxella catarrhalis* strain is *Moraxella catarrhalis* strain 4223.

13. The method of claim 12 wherein the cell lysate is fractionated by gel electrophoresis.

* * * * *

SEQUENCE LISTING

<160> NUMBER OF SEQ ID NOS: 4

<210> SEQ ID NO 1
<211> LENGTH: 6973
<212> TYPE: DNA
<213> ORGANISM: Moraxella catarrhalis

<400> SEQUENCE: 1

| | | | | | |
|---|---|---|---|---|---|
| ccatggatat | gggcaggtgt | gctcgcctgc | cgtatgatgg | cgatgacacc | ccatttgccc | 60 |
| catatctgta | cgatttgaca | tgtgatatga | tttaacatgt | gacatgattt | aacattgttt | 120 |
| aatactgttg | ccatcattac | cataatttag | taacgcattt | agtaacgcat | ttgtaaaaat | 180 |
| cattgcgccc | ctttatgtgt | atcatatgaa | tagaatatta | tgattgtatc | tgattattgt | 240 |
| atcagaatgg | tgatgctata | tgatgatgcc | tacgagttga | tttgggttaa | tcactctatg | 300 |
| atttgatata | ttttgaaact | aatctattga | cttaaatcac | catatggtta | taatttagca | 360 |
| taatggtagg | cttttgtaa | aaatcacatc | gcaatattgt | tctactgtta | ctaccatgct | 420 |
| tgaatgacga | tcccaatcac | cagattcatt | caagtgatgt | gtttgtatac | gcaccattta | 480 |
| ccctaattat | ttcaatcaaa | tgcctatgtc | agcatgtatc | atttttttaa | ggtaaaccac | 540 |
| catgaatcac | atctataaag | tcatctttaa | caaagccaca | ggcacattta | tggcagtggc | 600 |
| agagtacgcc | aaatcccaca | gcacgggggg | ggggtagctg | tgctacaggg | caagttggca | 660 |
| gtgtatgcac | tctgagcttt | gcccgtattg | ccgcgctcgc | tgtcctcgtg | atcggtgcaa | 720 |
| cgctcagtgg | cagtgcttat | gctcaaaaaa | aagataccaa | acatatcgca | attggtgaac | 780 |
| aaaaccagcc | aagacgctca | ggcactgcca | aggcggacgg | tgatcgagcc | attgctattg | 840 |
| gtgaaaatgc | taacgcacag | ggcggtcaag | ccatcgccat | cggtagtagt | aataaaactg | 900 |
| tcaatggaag | cagtttggat | aagataggta | ccgatgctac | gggtcaagag | tccatcgcca | 960 |
| tcggtggtga | tgtaaaggct | agtggtgatg | cctcgattgc | catcggtagt | gatgacttac | 1020 |
| atttgcttga | tcagcatggt | aatcctaaac | atccgaaagg | tactctgatt | aacgatctta | 1080 |
| ttaacggcca | tgcagtatta | aaagaaatac | gaagctcaaa | ggataatgat | gtaaaatata | 1140 |
| gacgcacaac | cgcaagcgga | cacgccagta | ctgcagtggg | agccatgtca | tatgcacagg | 1200 |
| gtcattttc | caacgccttt | ggtacacggg | caacagctaa | aagtgcctat | tccttggcag | 1260 |
| tgggtcttgc | cgccacagcc | gagggccaat | ctacaatcgc | tattggttct | gatgcaacat | 1320 |
| ctagctcgtt | gggagcgata | gcccttggtg | caggtactcg | tgctcagcta | cagggcagta | 1380 |
| ttgccctagg | tcaaggttct | gttgtcactc | agagtgataa | taattctaga | ccggcctata | 1440 |
| caccaaatac | ccaggcacta | gaccccaagt | ttcaagccac | caataatacg | aaggcgggtc | 1500 |
| cactttccat | tggtagtaac | tctatcaaac | gtaaaatcat | caatgtcggt | gcaggtgtta | 1560 |
| ataaaaccga | tgcggtcaat | gtggcacagc | tagaagcggt | ggtgaagtgg | gctaaggagc | 1620 |
| gtagaattac | ttttcaggt | gatgataaca | gtactgacgt | aaaaataggt | ttggataata | 1680 |
| ctttaactat | taaggtggt | gcagagacca | acgcattaac | cgataataat | atcggtgtgg | 1740 |
| taaaagaggc | tgataatagt | ggtctgaaag | ttaaacttgc | taaaacttta | aacaatctta | 1800 |
| ctgaggtgaa | tacaactaca | ttaaatgcca | caaccacagt | taaggtaggt | agtagtagta | 1860 |
| gtactacagc | tgaattattg | agtgatagtt | taaccttttac | ccagcccaat | acaggcagtc | 1920 |
| aaagcacaag | caaaaccgtc | tatggcgtta | atggggtgaa | gtttactaat | aatgcagaaa | 1980 |
| caacagcagc | aatcggcact | actcgtatta | ccagagataa | aattggcttt | gctcgagatg | 2040 |

-continued

```
gtgatgttga tgaaaaacaa gcaccatatt tggataaaaa acaacttaaa gtgggtagtg    2100
ttgcaattac catagacaat ggcattgatg caggtaataa aaagatcagt aatcttgcca    2160
aaggtagcag tgctaacgat gcggttacca tcgaacagct caaagccgcc aagcctactt    2220
taaacgcagg cgctggcatc agtgtcacac ctactgaaat atcagttgat gctaagagtg    2280
gcaatgttac cgcccccaact tacaacattg gcgtgaaaac caccgagctt aacagtgatg    2340
gcactagtga taaatttagt gttaagggta gtggtacgaa caatagctta gttaccgccg    2400
aacatttggc aagctatcta aatgaagtca atcgaacggc tgacagtgct ctacaaagct    2460
ttaccgttaa agaagaagac gatgatgacg ccaacgctat caccgtggct aaagatacga    2520
caaaaaatgc cggcgcagtc agcatcttaa aactcaaagg taaaaacggt ctaacggttg    2580
ctaccaaaaa agatggtacg gttacctttg gcttagcca agatagcggt ctgaccattg    2640
gcaaaagcac cctaaacaac gatggcttga ctgttaaaga taccaacgaa caaatccaag    2700
tcggtgctaa tggcattaaa tttactaatg tgaatggtag taatccaggt actggcattg    2760
caaataccgc tcgcattacc agagataaaa ttggctttgc tggttctgat ggtgcagttg    2820
atacaaacaa accttatctt gatcaagaca agctacaagt tggcaatgtt aagattacca    2880
acactggcat taacgcaggt ggtaaagcca tcacagggct gtccccaaca ctgcctagca    2940
ttgccgatca aagtagccgc aacatagaac tgggcaatac aatccaagac aaagacaaat    3000
ccaacgctgc cagcattaat gatatattaa atacaggctt taacctaaaa aataataaca    3060
accccattga ctttgtctcc acttatgaca ttgttgactt tgccaatggc aatgccacca    3120
ccgccacagt aacccatgat accgctaaca aaaccagtaa agtggtatat gatgtgaatg    3180
tggatgatac aaccattcat ctaacaggca ctgatgacaa taaaaaactt ggcgtcaaaa    3240 ccaccaaaact gaacaaaaca agtgctaatg gtaatacagc aactaacttt aatgttaact    3300
ctagtgatga agatgcccctt gttaacgcca aagacatcgc cgaaaatcta aacaccctag    3360
ccaaggaaat tcacaccacc aaaggcacag cagacaccgc cctacaaacc tttaccgtta    3420
aaaaggtaga tgaaataat aatgctgatg acgccaacgc catcaccgtg ggtcaaaaga    3480
acgcaaataa tcaagtcaac accctaacac tcaaggtga aaacggtctt aatattaaaa    3540
ccgacaaaaa tggtacggtt accttggca ttaacaccac aagcggtctt aaagccggca    3600
aaagcaccct aaacgacggt ggcttgtcta ttaaaaaccc cactggtagc gaacaaatcc    3660
aagtcggtgc tgatggcgtg aagtttgcca aggttaataa taatggtgtt gtaggtgctg    3720
gcattgatgg cacaactcgc attaccagag atgaaattgg ctttactggg actaatggct    3780
cacttgataa aagcaaaccc cacctaagca agacggcat taacgcaggt ggtaaaaaga    3840
ttaccaacat tcaatcaggt gagattgccc aaaacagcca tgatgctgtg acaggcggca    3900
agatttatga tttaaaaacc gaacttgaaa acaaaatcag cagtactgcc aaaacagcac    3960
aaaactcatt acacgaattc tcagtagcag atgaacaagg taataactttt acggttagta    4020 acccttactc cagttatgac acctcaaaga cctctgatgt catcaccttt gcaggtgaaa    4080
acggcattac caccaaggta aataaaggtg tggtgcgtgt gggcattgac caaaccaaag    4140
gcttaaccac gcctagctg accgtgggta ataataatgg caaaggcatt gtcattgaca    4200
gccaaaatgg tcaaaatacc atcacaggac taagcaacac tctagctaat gttaccaatg    4260
ataaaggtag cgtacgcacc acagaacagg gcaatataat caaagacgaa gacaaaaccc    4320
gtgccgccag cattgttgat gtgctaagcg caggctttaa cttgcaaggc aatggtgaag    4380
cggttgactt tgtctccact tatgacaccg tcaactttgc cgatggcaat gccaccaccg    4440
```

-continued

```
ctaaggtgac ctatgatgac acaagcaaaa ccagtaaagt ggtctatgat gtcaatgtgg    4500
atgatacaac cattgaagtt aaagataaaa aacttggcgt aaaaccacc acattgacca     4560 gtactggcac aggtgctaat aaatttgccc taagcaatca agctactggc gatgcgcttg    4620
tcaaggccag tgatatcgtt gctcatctaa acaccttatc tggcgacatc caaactgcca    4680
aaggggcaag ccaagcgaac aactcagcag gctatgtgga tgctgatggc aataaggtca    4740
tctatgacag taccgataac aagtactatc aagccaaaaa tgatggcaca gttgataaaa    4800
ccaaagaagt tgccaaagac aaactggtcg cccaagccca accccagat ggcacattgg     4860 ctcaaatgaa tgtcaaatca gtcattaaca aagaacaagt aaatgatgcc aataaaaagc    4920
aaggcatcaa tgaagacaac gcctttgtta aaggacttga aaaagccgct tctgataaca    4980
aaaccaaaaa cgccgcagta actgtgggtg atttaaatgc cgttgcccaa acaccgctga    5040
cctttgcagg ggatacaggc acaacggcta aaaaactggg cgagactttg accatcaaag    5100
gtgggcaaac agacaccaat aagctaaccg ataataacat cggtgtggta gcaggtactg    5160
atggcttcac tgtcaaactt gccaaagacc taaccaatct taacagcgtt aatgcaggtg    5220
gcaccaaaat tgatgacaaa ggcgtgtctt ttgtagactc aagcggtcaa gccaaagcaa    5280
acacccctgt gctaagtgcc aatgggctgg acctgggtgg caaggtcatc agtaatgtgg    5340
gcaaaggcac aaaagatacc gacgctgcca atgtacaaca gttaaacgaa gtacgcaact    5400
tgttgggtct tggtaatgct ggtaatgata acgctgacgg caatcaggta acattgccg     5460 acatcaaaaa agacccaaat tcaggttcat catctaaccg cactgtcatc aaagcaggca    5520
cggtacttgg cggtaaaggt aataacgata ccgaaaaact tgccactggt ggtatacaag    5580
tgggcgtgga taaagacggc aacgctaacg gcgatttaag caatgtttgg gtcaaaaccc    5640
aaaaagatgg cagcaaaaaa gccctgctcg ccacttataa cgccgcaggt cagaccaact    5700
atttgaccaa caacccgca gaagccattg acagaataaa tgaacaaggt atccgcttct     5760
tccatgtcaa cgatggcaat caagagcctg tggtacaagg gcgtaacggc attgactcaa    5820
gtgcctcagg caagcactca gtggcgatag gtttccaggc caaggcagat ggtgaagccg    5880
ccgttgccat aggcagacaa acccaagcag gcaaccaatc catcgccatc ggtgataacg    5940
cacaagccac gggcgatcaa tccatcgcca tcggtacagg caatgtggta gcaggtaagc    6000
actctggtgc catcggcgac ccaagcactg ttaaggctga taacagttac agtgtgggta    6060
ataacaacca gttaccgat gccactcaaa ccgatgtctt tggtgtgggc aataacatca     6120
ccgtgaccga agtaactcg gttgccttag gttcaaactc tgccatcagt gcaggcacac      6180
acgcaggcac acaagccaaa aaatctgacg gcacagcagg tacaaccacc acagcaggtg    6240
caaccggtac ggttaaaggc tttgctggac aaacggcggt tggtgcggtc tccgtgggtg    6300
cctcaggtgc tgaacgccgt atccaaaatg tggcagcagg tgaggtcagt gccaccagca    6360
ccgatgcggt caatggtagc cagttgtaca agccaccca agcattgcc aacgcaacca     6420 atgagcttga ccatcgtatc caccaaaacg aaaataaggc caatgcaggg atttcatcag    6480
cgatggcgat ggcgtccatg ccacaagcct acattcctgg cagatccatg gttaccgggg    6540
gtattgccac ccacaacggt caaggtgcgg tggcagtggg actgtcgaag ctgtcggata    6600
atggtcaatg ggtatttaaa atcaatggtt cagccgatac ccaaggccat gtaggggcgg    6660
cagttggtgc aggttttcac ttttaagcca taaatcgcaa gatttacttt aaaaatcaat    6720
ctcaccatag ttgtataaaa cagcatcagc atcagtcata ttactgatgc tgatgttttt    6780
tatcacttaa accattttac cgctcaagtg attctctttc accatgacca aatcgccatt    6840
```

```
-continued gatcataggt aaacttattg agtaaatttt atcaatgtag ttgttagata tggttaaaat    6900
tgtgccattg accaaaaaat gaccgattta tcccgaaaat ttctgattat gatccgttga    6960
cctgcaggtc gac                                                       6973

<210> SEQ ID NO 2
<211> LENGTH: 20
<212> TYPE: PRT
<213> ORGANISM: Moraxella catarrhalis
<220> FEATURE:
<221> NAME/KEY: UNSURE
<222> LOCATION: (17)

<400> SEQUENCE: 2

Asn Val Lys Ser Val Ile Asn Lys Glu Gln Val Asn Asp Ala Asn Lys
 1               5                  10                  15

Xaa Gln Gly Ile
            20

<210> SEQ ID NO 3
<211> LENGTH: 16
<212> TYPE: PRT
<213> ORGANISM: Moraxella catarrhalis

<400> SEQUENCE: 3

Asn Val Lys Ser Val Ile Asn Lys Glu Gln Val Asn Asp Ala Asn Lys
 1               5                  10                  15

<210> SEQ ID NO 4
<211> LENGTH: 60
<212> TYPE: DNA
<213> ORGANISM: Moraxella catarrhalis

<400> SEQUENCE: 4
aatgtcaaat cagtcattaa caaagaacaa gtaaatgatg ccaataaaaa gcaaggcatc     60
```